US010892055B2

(12) United States Patent
Sato et al.

(10) Patent No.: US 10,892,055 B2
(45) Date of Patent: Jan. 12, 2021

(54) MOTOR FUNCTION ESTIMATION INFORMATION GENERATION APPARATUS, MOTOR FUNCTION ESTIMATION SYSTEM, MOTOR FUNCTION ESTIMATION INFORMATION GENERATION METHOD, MOTOR FUNCTION ESTIMATION METHOD AND STORAGE MEDIUM

(71) Applicant: Panasonic Intellectual Property Management Co., Ltd., Osaka (JP)

(72) Inventors: Yoshikuni Sato, Osaka (JP); Toru Nakada, Kyoto (JP); Yoshihide Sawada, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 834 days.

(21) Appl. No.: 15/666,950

(22) Filed: Aug. 2, 2017

(65) Prior Publication Data
US 2018/0060511 A1    Mar. 1, 2018

(30) Foreign Application Priority Data

Aug. 24, 2016 (JP) ................ 2016-163765
Jul. 21, 2017 (JP) ................ 2017-142290

(51) Int. Cl.
*G06N 3/04* (2006.01)
*G16H 50/20* (2018.01)
(Continued)

(52) U.S. Cl.
CPC .......... *G16H 50/20* (2018.01); *G06N 3/0436* (2013.01); *G06N 3/08* (2013.01); *G16H 20/30* (2018.01);
(Continued)

(58) Field of Classification Search
CPC ...... G06N 3/0436; G06N 3/08; G06N 3/0445; G06N 3/0472; G16H 50/20; G16H 20/30; G16H 40/63
See application file for complete search history.

(56) References Cited

U.S. PATENT DOCUMENTS 8,840,569 B2 * 9/2014 Flaction ............ G06K 9/00342
600/587
10,046,229 B2 * 8/2018 Tran ........................ B33Y 10/00
(Continued)

FOREIGN PATENT DOCUMENTS

JP    2006-320533       11/2006
JP    2006320533 A  *  11/2006
WO    WO-2016194908 A1 * 12/2016 ............. A61B 5/224

OTHER PUBLICATIONS

Plotz et al., "Feature Learning for Activity Recognition in Ubiquitous Computing", Jul. 2011, Proceedings of Twenty-Second International Joint Conference on Artificial Intelligence, pp. 1729-1734. (Year: 2011).*
(Continued)

*Primary Examiner* — Paulinho E Smith
(74) *Attorney, Agent, or Firm* — Wenderoth, Lind & Ponack, L.L.P.

(57) ABSTRACT

An apparatus generates motor function estimation information by performing a process including calculating, using a sensor value of a subject, a feature vector corresponding to a feature value of a feature in a time segment, acquiring a first weight vector using the feature vector and a motor ability value of the subject, calculating a gradient vector with respect to the feature vector, determining a new time segment in the predetermined time period and a new feature value based on the new time segment, calculating, using the sensor value, a feature candidate vector corresponding to a feature value of the new feature in the new time segment,
(Continued)

determining a feature candidate vector satisfying a predetermined condition associated with a gradient vector based on a difference between the feature candidate vector and the feature vector, and correcting the first weight vector to a second weight vector using the feature candidate vector.

17 Claims, 10 Drawing Sheets

(51) Int. Cl.
  *G06N 3/08* (2006.01)
  *G16H 20/30* (2018.01)
  *G16H 40/63* (2018.01)
(52) U.S. Cl.
  CPC .......... *G16H 40/63* (2018.01); *G06N 3/0445* (2013.01); *G06N 3/0472* (2013.01)

(56) References Cited

U.S. PATENT DOCUMENTS

| | | | |
|---|---|---|---|
| 10,357,195 B2* | 7/2019 | Beck | A61B 5/18 |
| 10,391,360 B2* | 8/2019 | Flaction | A63B 24/0062 |
| 10,702,168 B2* | 7/2020 | Morikawa | A61B 5/0452 |
| 2017/0056725 A1* | 3/2017 | Nakada | A61B 5/0205 |
| 2018/0047388 A1* | 2/2018 | Tyagi | G10L 15/16 |
| 2018/0055446 A1* | 3/2018 | Sato | A61B 5/02438 |
| 2018/0060511 A1* | 3/2018 | Sato | G06N 3/0436 |
| 2020/0051254 A1* | 2/2020 | Habibian | G06T 7/251 |

OTHER PUBLICATIONS

Thomas Plotz et al., "Feature Learning for Activity Recognition in Ubiquitous Computing", Proceedings of the Twenty-Second International Joint Conference on Artificial Intelligence, pp. 1729-1734, Jul. 2011.

* cited by examiner

FIG. 5

| FEATURE NUMBER | TIME SEGMENT | | FEATURE TO BE EXTRACTED |
| --- | --- | --- | --- |
| | START (sec) | END (sec) | |
| 1 | 0 | 30 | COEFFICIENT OF 1st MAIN COMPONENT OF PCA |
| 2 | 0 | 30 | COEFFICIENT OF 2nd MAIN COMPONENT OF PCA |
| 3 | 0 | 30 | COEFFICIENT OF 3rd MAIN COMPONENT OF PCA |
| ... | ... | ... | ... |
| 32 | 0 | 30 | COEFFICIENT OF 32nd MAIN COMPONENT OF PCA |

FIG. 7

| FEATURE NUMBER | TIME SEGMENT | | FEATURE TO BE EXTRACTED |
| --- | --- | --- | --- |
| | START (sec) | END (sec) | |
| 1 | 0 | 30 | COEFFICIENT OF 1st MAIN COMPONENT OF PCA |
| 2 | 15 | 45 | COEFFICIENT OF 5th MAIN COMPONENT OF PCA |
| 3 | 0 | 30 | COEFFICIENT OF 3rd MAIN COMPONENT OF PCA |
| ... | ... | ... | ... |
| 32 | 30 | 60 | COEFFICIENT OF 2nd MAIN COMPONENT OF PCA |

| FEATURE NUMBER | CORRELATION WITH MEASURED VALUE | AVERAGE RELATIVE ERROR |
|---|---|---|
| WALK DISTANCE IN 6 MINUTES, WALK SPEED FOR 10 m | 0.68 | 0.199 |
| FIXED FEATURE VALUE (OVERALL WALK PCA) | 0.74 | 0.174 |
| PRESENT EMBODIMENT | 0.85 | 0.137 |

MOTOR FUNCTION ESTIMATION INFORMATION GENERATION APPARATUS, MOTOR FUNCTION ESTIMATION SYSTEM, MOTOR FUNCTION ESTIMATION INFORMATION GENERATION METHOD, MOTOR FUNCTION ESTIMATION METHOD AND STORAGE MEDIUM

BACKGROUND

1. Technical Field

The present disclosure relates to a motor function estimation information generation apparatus that estimates a motor function, a motor function estimation system, a motor function estimation information generation method, a motor function estimation method, and a storage medium.

2. Description of the Related Art

Information on motor functions, in particular information on a walking function or the like is important to determine details of a rehabilitation to be performed on a person. In recent years, there has been a social problem due to sarcopenia or a weakened walking function, which may cause a person to fall down. Thus, there is an increasing need for a technique that allows it to easily and accurately evaluate a walking ability of a person. Roughly speaking, the walking ability has three factors, that is, a muscle strength, an endurance, and a balancing ability. To accurately measure these abilities physiotherapeutically, an isokinetic strength measurement instrument, a cardiopulmonary exercise testing instrument, and a stabilometer may be used. Although these instruments and the test using these instruments can provide an accurate result, the instruments may be complicated, and a large burden may be imposed on a subject during measurement. Therefore, this method is not suitable for evaluating a motor function of a type occurring in a daily life. To solve the above problem, in a technique disclosed in Japanese Patent No. 4696677, an average acceleration in a vertical direction and an average acceleration in a horizontal back-and-forth direction are calculated as feature values from values detected by an acceleration sensor worn on a waist of a person, and a lower extremity muscle strength is estimated from the calculated feature values. A technique of extracting a feature for behavior recognition is disclosed in Thomas Plotz et, al, "Feature Learning for Activity Recognition in Ubiquitous Computing", International Joint Conference on Artificial Intelligence, IJCAI, 2011, p. 1729.

SUMMARY

However, in the technique disclosed in Japanese Patent No. 4696677, an average acceleration value, a maximum acceleration value, and a minimum acceleration value are used as features, but a feature of a waveform of the measured acceleration is not substantially used. As a result, the technique disclosed in Japanese Patent No. 4696677 has a problem that it is difficult to achieve a high accuracy in estimating a lower extremity muscle strength. Although there is a technique of generating a feature for behavior recognition in machine learning as disclosed, for example, in Thomas Plotz et. al, "Feature Learning for Activity Recognition in Ubiquitous Computing", International Joint Conference on Artificial Intelligence, IJCAI, 2011, p. 1729, such a conventional technique captures a feature in sensor data with a length as short as several seconds, and thus it is difficult to automatically calculate a useful feature from sensor data with a length as large as several minutes to several hours or longer.

One non-limiting and exemplary embodiment provides a motor function estimation information generation apparatus, a motor function estimation system, a motor function estimation information generation method, a motor function estimation method, and a storage medium, capable of providing improved accuracy in estimating a motor function from long-time sensor data.

In one general aspect, the techniques disclosed here feature a motor function estimation information generation apparatus including a sensor that measures, in a predetermined time period, at least one selected from the group consisting of an acceleration, a heart rate, a body temperature, and an angular velocity of a subject, and a first processing circuit that performs a process, the process performed by the first processing circuit including (a1) acquiring at least one sensor value selected from the group consisting of sensor values in terms of the acceleration, the heart rate, the body temperature, and the angular velocity of the subject, and a motor ability value of the subject, (a2) determining a feature of the sensor value and a time segment in the predetermined time period, (a3) calculating, using the sensor value, a feature vector corresponding to a feature value of the feature in the time segment, (a4) acquiring a first weight vector for use in estimating a motor ability value using the feature vector and the motor ability value, (a5) calculating a gradient vector with respect to the feature vector using the first weight vector and the motor ability value, (a6) determining a new time segment in the predetermined time period and a new feature based on the new time segment, (a7) calculating, using the sensor value, a feature candidate vector that is a candidate for a feature vector corresponding to a feature value of the new feature in the new time segment, (a8) determining a feature candidate vector satisfying a predetermined condition based on the gradient vector, based on a difference between the feature candidate vector and the feature vector, (a9) correcting the first weight vector to a second weight vector using the feature candidate vector satisfying the predetermined condition, and (a10) storing, in a storage, a feature and a time segment corresponding to the feature candidate vector satisfying the predetermined condition and also storing the second weight vector.

The present disclosure makes it possible to improve the accuracy in estimating a motor function from a long-time sensor data.

It should be noted that general or specific embodiments may be implemented as a system, a method, an integrated circuit, a computer program, a computer-readable storage medium, or any selective combination thereof. The computer-readable storage medium may be a non-transitory storage medium such as a CD-ROM (Compact Disc-Read Only Memory) or the like.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram illustrating an example of a combination of a time segment and an initial value of a feature to be extracted;

FIG. 7 is a diagram illustrating an example of a combination of an updated time segment and a feature to be extracted;

DETAILED DESCRIPTION

Figure 1:
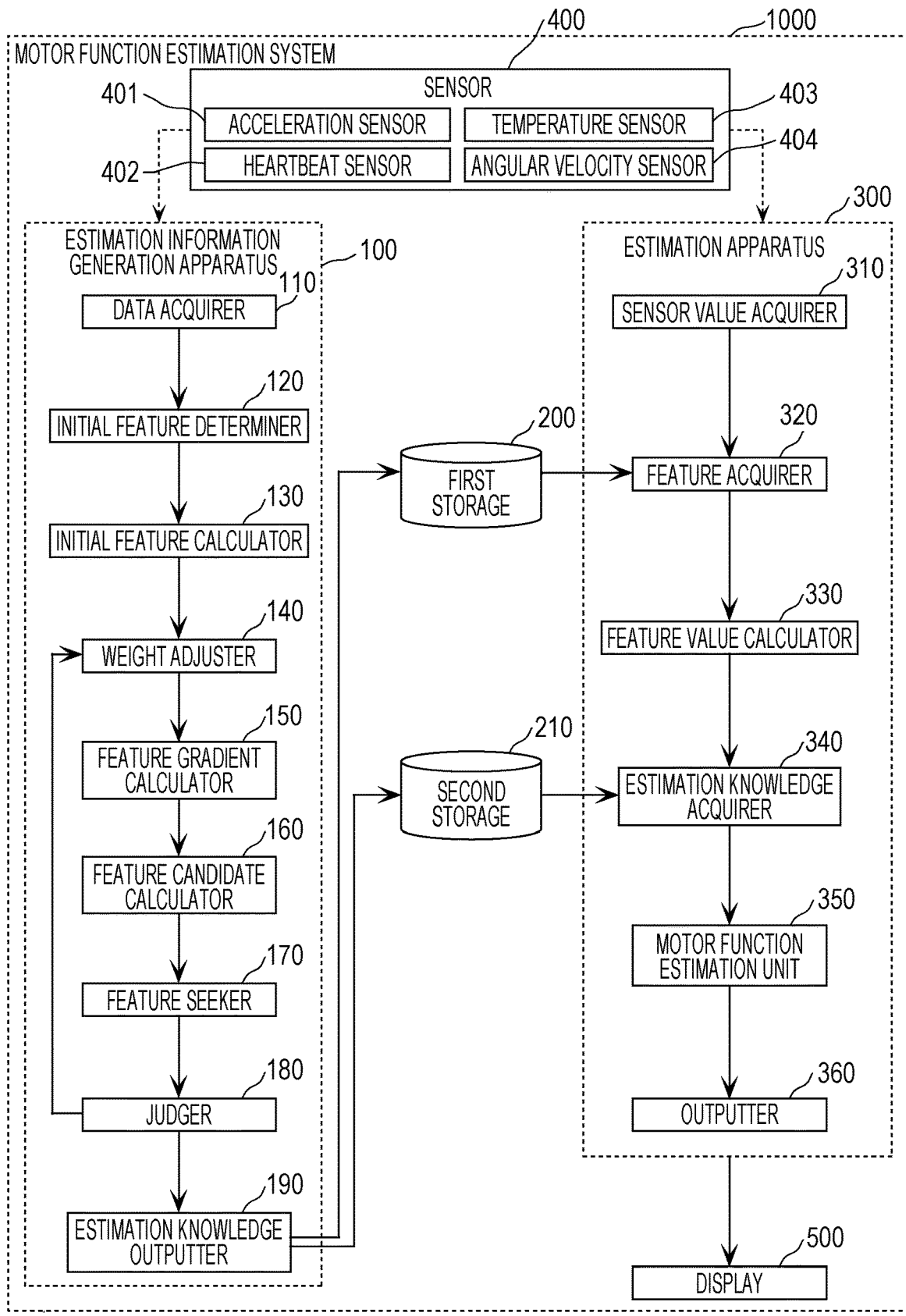
FIG. 1 is a block diagram illustrating a configuration of a motor function estimation system according to an embodiment.

The inventors associated with the present disclosure (hereinafter referred to as the present inventors) have investigated the techniques described in section "2. Description of the Related Art", that is, the technique disclosed in Japanese Patent No. 4696677 and the technique disclosed in Thomas Plotz et. al, "Feature Learning for Activity Recognition in Ubiquitous Computing", International Joint Conference on Artificial Intelligence, IJCAI, 2011, p. 1729, and further investigated a technique for improving accuracy in estimating a motor function. In the technique disclosed in Japanese Patent No. 4696677, a feature extracted from sensor data output from a sensor worn on a subject is used in estimating a motor function of the subject. However, in the technique disclosed in Japanese Patent No. 4696677, measured data is not sufficiently reflected in the extracted feature value, which may cause a reduction in accuracy in estimating the motor function. The present inventors have found the fact that estimation accuracy of a motor function can be affected by a feature extracted from sensor data, and the present inventors have investigated a technique for finding a useful feature. On the other hand, in the technique disclosed in Thomas Plotz et, al, "Feature Learning for Activity Recognition in Ubiquitous Computing", International Joint Conference on Artificial Intelligence, IJCAI, 2011, p. 1729, although a technique for generating a feature using machine learning is described, input data itself is input to machine learning but data obtained during a long measurement period is not input. In view of the above, the present inventors have established a technique in which a feature useful for motor function estimation is extracted from sensor data obtained in a long measurement period, and high accuracy is achieved in the motor function estimation using the sensor data obtained in the long measurement period as described in detail below.

In an aspect, the present disclosure provides a motor function estimation information generation apparatus including a sensor that measures, in a predetermined time period, at least one selected from the group consisting of an acceleration, a heart rate, a body temperature, and an angular velocity of a subject, and a first processing circuit. The first processing circuit described above performs a process including (a1) acquiring at least one sensor value selected from the group consisting of sensor values in terms of the acceleration, the heart rate, the body temperature, and the angular velocity of the subject, and a motor ability value of the subject, (a2) determining an initial feature of the sensor value and a time segment in the predetermined time period, (a3) calculating, using the sensor value, a feature vector corresponding to the initial feature in the time segment, (a4) acquiring a first weight vector for use in estimating a motor ability value using the feature vector and the motor ability value, (a5) calculating a gradient vector with respect to the feature vector using the first weight vector and the motor ability value, (a6) determining a new feature and a new time segment in the predetermined time period, (a7) calculating, using the sensor value, a feature candidate vector that is a candidate for a feature vector corresponding to the new feature in the new time segment, (a8) determining a feature candidate vector satisfying a predetermined condition based on the gradient vector, based on a difference between the feature candidate vector and the feature vector, (a9) correcting the first weight vector to a second weight vector using the feature candidate vector satisfying the predetermined condition, and (a10) storing, in a storage, a feature and a time segment corresponding to the feature candidate vector satisfying the predetermined condition and also storing the second weight vector.

In this aspect, when a feature vector is updated to a more proper feature candidate vector, a weight vector is updated to a more proper weight vector using the updated feature candidate vector. Such a weight vector implements estimation knowledge for estimating a motor ability value. Use of such estimation knowledge makes it possible to extract an optimum feature vector and a time segment for the input sensor value and output a motor ability value based on the extracted feature vector and the time segment. Thus, the motor function estimation information generation apparatus is capable of outputting an optimum motor ability value also in a case where a sensor value obtained for a long measurement time is used.

In the motor function estimation information generation apparatus according to the aspect of the present disclosure, the weight vector may implement a neural network such that a connection between nodes of the neural network is weighted by the weight vector. In the aspect described above, the machine learning using the neural network makes it possible to enhance the accuracy in estimation based on input information with respect to a correct answer. Furthermore, use of the neural network makes it possible to reduce the processing complexity in obtaining an estimation result even when a large number of pieces of input information is given, that is, even in a case where there are a large number of input nodes.

In the motor function estimation information generation apparatus according to the aspect of the present disclosure, the gradient vector may be a gradient vector with respect to the feature vector in terms of an index indicating an error of the motor ability value estimated using the first weight vector from the acquired actual motor ability value. In the aspect described above, the gradient vector indicates a gradient with which the error changes as the feature vector changes. For example, by determining the feature candidate vector such that when the feature vector is changed to the feature candidate vector in a direction of the gradient vector which results in a smaller error, the second weight vector based on this feature candidate vector can implement estimation knowledge with higher accuracy than can be achieved by the first weight vector.

In the motor function estimation information generation apparatus according to the aspect of the present disclosure, the feature candidate vector satisfying the predetermined condition may be determined based on a degree of coincidence of the difference between the feature candidate vector and the feature vector with the gradient vector. In the aspect described above, the feature candidate vector satisfying the predetermined condition may be determined such that the difference between the feature candidate vector and the feature vector has a correlation with the gradient vector. Note that it is easy to determine the feature candidate vector in the manner described above.

In an aspect, the present disclosure provides a motor function estimation system including the motor function estimation information generation apparatus described above and a second processing circuit. The second processing circuit acquiring at least on sensor value selected from the group consisting of sensor values in terms of an acceleration, a heart rate, a body temperature, and an angular velocity of a subject, calculating an estimated feature vector using a feature and a time segment stored in the storage and the sensor value. The second processing circuit then estimates a motor ability value using the second weight vector stored in the storage and the estimated feature vector, and outputs the resultant motor ability value.

According to the aspect described above, the motor function estimation system is capable of outputting a motor ability value using the estimation knowledge of the motor function estimation information generation apparatus such that the motor ability value indicates a most reasonable value for the input sensor value.

In an aspect, the present disclosure provides a motor function estimation information generation method including (b1) acquiring at least one sensor value selected from the group consisting of sensor values in terms of an acceleration, a heart rate, a body temperature, and an angular velocity of a subject, and a motor ability value of the subject, (b2) determining an initial feature of the sensor value and a time segment in a predetermined time period, (b3) calculating, using the sensor value, a feature vector corresponding to the initial feature in the time segment, (b4) acquiring a first weight vector for use in estimating a motor ability value using the feature vector and the motor ability value, (b5) calculating a gradient vector with respect to the feature vector using the first weight vector and the motor ability value, (b6) determining a new feature and a new time segment in the predetermined time period, (b7) calculating, using the sensor value, a feature candidate vector that is a candidate for a feature vector corresponding to the new feature in the new time segment, (b8) determining a feature candidate vector satisfying a predetermined condition based on the gradient vector, based on a difference between the feature candidate vector and the feature vector, and (b9) correcting the first weight vector to a second weight vector using the feature candidate vector satisfying the predetermined condition.

According to the aspect described above, it is possible to achieve effects similar to those achieved by the motor function estimation information generation apparatus according to the previous aspect of the present disclosure.

In the motor function estimation information generation method according to the aspect of the present disclosure, the weight vector may implement a neural network such that a connection between nodes of the neural network is weighted by the weight vector.

In the motor function estimation information generation method according to the present aspect of the disclosure, the gradient vector may be a gradient vector with respect to the feature vector in terms of an index indicating an error of the motor ability value estimated using the first weight vector from the acquired actual motor ability value.

In the motor function estimation information generation method according to the present aspect of the disclosure, the feature candidate vector satisfying the predetermined condition may be determined based on a degree of coincidence of the difference between the feature candidate vector and the feature vector with the gradient vector.

In an aspect, the present disclosure provides a motor function estimation method including (b1) acquiring at least one sensor value selected from the group consisting of sensor values in terms of an acceleration, a heart rate, a body temperature, and an angular velocity of a subject, and a motor ability value of the subject, (b2) determining an initial feature value of the sensor value and a time segment in a predetermined time period, (b3) calculating, using the sensor value, a feature vector corresponding to the initial feature value in the time segment, (b4) acquiring a first weight vector for use in estimating a motor ability value using the feature vector and the motor ability value, (b5) calculating a gradient vector with respect to the feature vector using the first weight vector and the motor ability value, (b6) determining a new feature value and a new time segment in the predetermined time period, (b7) calculating, using the sensor value, a feature candidate vector that is a candidate for a feature vector corresponding to the new feature value in the new time segment, (b8) determining a feature candidate vector satisfying a predetermined condition based on the gradient vector, based on a difference between the feature candidate vector and the feature vector, (b9) correcting the first weight vector to a second weight vector using the feature candidate vector satisfying the predetermined condition, (b10) storing, in a storage, a feature value and a time segment corresponding to the feature candidate vector satisfying the predetermined condition and also storing the second weight vector, (b11) further acquiring at least one sensor value selected from the group consisting of sensor values in terms of an acceleration, a heart rate, a body temperature, and an angular velocity of a subject, (b12) calculating an estimated feature vector using the sensor value and the feature value and the time segment stored in the storage, and (b13) estimating a motor ability value using the second weight vector stored in the storage and the estimated feature vector.

According to the aspect described above, it is possible to achieve effects similar to those achieved by the motor function estimation system according to the previous aspect of the present disclosure.

In an aspect, the present disclosure provides a storage medium including a stored control program for causing a device having a processor to execute a process, the storage medium being non-transitory and computer-readable, the process including (b1) acquiring at least one sensor value selected from the group consisting of sensor values in terms of an acceleration, a heart rate, a body temperature, and an angular velocity of a subject, and a motor ability value of the subject, (b2) determining an initial feature of the sensor value and a time segment in a predetermined time period, (b3) calculating, using the sensor value, a feature vector corresponding to the initial feature in the time segment, (b4) acquiring a first weight vector for use in estimating a motor ability value, using the feature vector and the motor ability value, (b5) calculating a gradient vector with respect to the feature vector using the first weight vector and the motor ability value, (b6) determining a new feature and a new time segment in the predetermined time period, (b7) calculating, using the sensor value, a feature candidate vector that is a candidate for a feature vector corresponding to the new feature in the new time segment, (b8) determining a feature candidate vector satisfying a predetermined condition based on the gradient vector, based on a difference between the feature candidate vector and the feature vector, (b9) correcting the first weight vector to a second weight vector using the feature candidate vector satisfying the predetermined condition, and (b10) storing, in a storage, a feature and a time segment corresponding to the feature candidate vector satisfying the predetermined condition and also storing the second weight vector.

According to the aspect described above, it is possible to achieve effects similar to those achieved by the motor function estimation information generation apparatus according to the previous aspect of the present disclosure.

In the storage medium according to the present aspect of the disclosure, the weight vector may implement a neural network such that a connection between nodes of the neural network is weighted by the weight vector.

In the storage medium according to the present aspect of the disclosure, the gradient vector may be a gradient vector with respect to the feature vector in terms of an index indicating an error of the motor ability value estimated using the first weight vector from the acquired actual motor ability value.

In the storage medium according to the present aspect of the disclosure, the feature candidate vector satisfying the predetermined condition may be determined based on a degree of coincidence of the difference between the feature candidate vector and the feature vector with the gradient vector.

In an aspect, the present disclosure provides a storage medium including a stored control program for causing a device having a processor to execute a process, the storage medium being non-transitory and computer-readable, the process including (b1) acquiring at least one sensor value selected from the group consisting of sensor values in terms of an acceleration, a heart rate, a body temperature, and an angular velocity of a subject, and a motor ability value of the subject, (b2) determining an initial feature of the sensor value and a time segment in a predetermined time period, (b3) calculating, using the sensor value, a feature vector corresponding to the initial feature in the time segment, (b4) acquiring a first weight vector for use in estimating a motor ability value using the feature vector and the motor ability value, (b5) calculating a gradient vector with respect to the feature vector using the first weight vector and the motor ability value, (b6) determining a new feature and a new time segment in the predetermined time period, (b7) calculating, using the sensor value, a feature candidate vector that is a candidate for a feature vector corresponding to the new feature in the new time segment, (b8) determining a feature candidate vector satisfying a predetermined condition based on the gradient vector, based on a difference between the feature candidate vector and the feature vector, (b9) correcting the first weight vector to a second weight vector using the feature candidate vector satisfying the predetermined condition, (b10) storing, in a storage, a feature and a time segment corresponding to the feature candidate vector satisfying the predetermined condition and also storing the second weight vector, (b11) further acquiring at least one sensor value selected from the group consisting of sensor values in terms of an acceleration, a heart rate, a body temperature, and an angular velocity of a subject, (b12) calculating an estimated feature vector using the feature and the time segment stored in the storage and the sensor value, and (b13) estimating a motor ability value using the second weight vector stored in the storage and the estimated feature vector.

In this aspect, it is possible to achieve effects similar to those achieved by the motor function estimation system according to the previous aspect of the present disclosure.

A motor function estimation system and related techniques according to an embodiment is described below with reference to drawings. Note that any embodiment described below is provided to illustrate a general or specific example. In the following embodiments of the present disclosure, values, shapes, constituent elements, locations of elements, manners of connecting elements, steps, the order of steps, and the like are described by way of example but not limitation. Among constituent elements described in the following embodiments, those constituent elements that are not described in independent claims indicating highest-level concepts of the present disclosure are optional. In the following description of embodiments, "nearly", "substantially", or "about" may be used to describe a property of some element. For example, when it is described that somethings are "nearly parallel", this means that they are absolutely parallel or nearly parallel. That is, a difference within a few percent is allowed. This also applied to other similar expressions using "about", "substantially", or the like. Embodiments 1. Configuration of Motor Function Estimation System According to an Embodiment First, referring to FIG. 1, a configuration of a motor function estimation system 1000 according to an embodiment is described below. FIG. 1 is a block diagram illustrating the configuration of the motor function estimation system 1000 according to the embodiment. The motor function estimation system 1000 estimates a state of a motor function of a subject, such as a motor ability value, from a measurement result provided by a sensor worn on a subject. Note that in the present description, a subject refers to a person subjected to a test for the estimation.

As illustrated in FIG. 1, the motor function estimation system 1000 includes an estimation information generation apparatus 100, a first storage 200, a second storage 210, an estimation apparatus 300, a sensor 400, and a display 500. The motor function estimation system 1000 may be configured with one apparatus or two or more apparatuses. Part or all of the motor function estimation system 1000 may be embedded in an apparatus such that the motor function estimation system 1000 functions as a part of the apparatus. Of the estimation information generation apparatus 100, the first storage 200, the second storage 210, and the estimation apparatus 300, at least the estimation information generation apparatus 100 may form a motor function estimation apparatus.

The estimation information generation apparatus 100 implements estimation knowledge for use in estimating an ability value indicating a motor function of a subject from a measurement result provided by the sensor 400. For example, the estimation information generation apparatus 100 implements estimation knowledge for use in machine learning. In the present embodiment, the estimation information generation apparatus 100 extracts a time segment to be used in the estimation and a feature to be calculated, as estimation knowledge for use in estimating a motor function of a subject from an action sensor value of a subject in a predetermined time period, and the estimation information generation apparatus 100 calculates a relationship between the calculated feature and a motor ability value. Note that the action sensor value of the subject includes the measurement result provided by the sensor 400 worn on the subject. For example, the action sensor value may include a measured value associated with a measurement time. The estimation information generation apparatus 100 includes a data acquirer 110, an initial feature determiner 120, an initial feature calculator 130, a weight adjuster 140, a feature gradient calculator 150, a feature candidate calculator 160, a feature seeker 170, a judger 180, and an estimation knowledge outputter 190.

Using the estimation knowledge implemented by the estimation information generation apparatus 100, the estimation apparatus 300 estimates a motor function of a subject from an action sensor value acquired using the sensor 400. The estimation apparatus 300 includes a sensor value acquirer 310, a feature acquirer 320, a feature value calculator 330, an estimation knowledge acquirer 340, a motor function estimator 350, and an outputter 360.

The estimation information generation apparatus 100 and the estimation apparatus 300 may be realized using hardware such as a circuit, an integrated circuit, or the like including constituent elements described above or may be realized using software such as a program or the like executed on a computer. For example, the constituent elements may be realized by a computer system (not illustrated) such as a CPU (Central Processing Unit), a RAM (Random Access Memory), a ROM (Read-Only Memory), or the like. Part of all of the functions of the constituent elements described above may be achieved by a CPU executing a program stored in a ROM using a RAM as a work memory. The program may be a program provided as an application via a communication using a communication network such as the Internet or via a communication according to a mobile communication standard, or the like.

The estimation information generation apparatus 100 and the estimation apparatus 300 may form one constituent element or separate constituent elements. The estimation information generation apparatus 100 and the estimation apparatus 300 may be realized, for example, by a CPU, an MPU (Micro Processing Unit), a CPU, a processor, a circuit such as an LSI (Large Scale Integration), an IC card (Integrated Circuit Card), a module, or the like.

Figure 2:
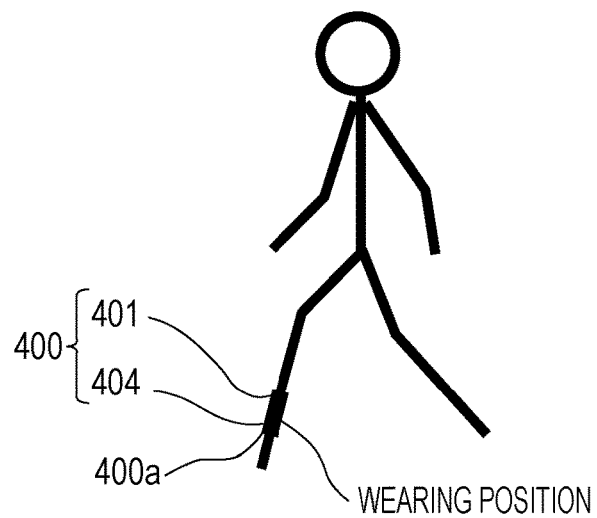
FIG. 2 is a diagram illustrating an example of a position where each of an acceleration sensor and an angular velocity sensor shown in FIG. 1 is worn on a subject.

The estimation information generation apparatus 100 and the estimation apparatus 300 may be disposed together with the sensor 400 on a band 400a shown in FIG. 2, and may perform a wired or wireless communication with the display 500 or an apparatus including the display 500. Alternatively, the estimation information generation apparatus 100 and the estimation apparatus 300 may be disposed at a location apart from the sensor 400 and may perform a wired or wireless communication with the sensor 400. In this case, the estimation information generation apparatus 100 and the estimation apparatus 300 may be realized in the form of a separate module or may be disposed in another apparatus such as a computer or the like. As for the wired communication described above, any known wired communication technique may be used. Similarly, as for the wireless communication described above, any known wireless communication technique may be used. For example, the wireless communication may be realized using a wireless LAN (Local Area Network) system such as a Wi-Fi® system or a short distance communication system such as near field communication (NFC), Bluetooth®, ZigBee®, or the like.

Sensor 400

The sensor 400 is worn on a subject, and acquires an action value of a subject as a measurement result and outputs it. An example of an action value is a parameter selected from the group of parameters including an acceleration, a heart rate, a body temperature, an angular velocity, and/or the like measured during a subject's operation in a daily life or during a motor test such as a 6-minute walk test performed on the subject. Note that the 6-minute walk test (6MWT) is a constant load test in which is a subject is supposed to walk at a constant speed. More specifically, a subject walks as fast as possible for 6 minutes, and an exercise tolerance of the subject is evaluated based on an achieved walking distance.

The sensor 400 may be configured to output a measurement result including an action value of a subject and an ID of the subject associated with each other. For example, the sensor 400 may be configured to have an input unit such that a subject is allowed to input a subject's ID via the input unit thereby allowing the sensor 400 to acquire the subject's ID. For example, the input unit may be a touch panel or a keypad including keys of characters and/or numerals. The sensor 400 may be configured to communicate with the estimation information generation apparatus 100 and the estimation apparatus 300 wirelessly or with a cable such that a value measured by the sensor 400 (hereinafter also referred to as a sensor value) is transmitted to the estimation information generation apparatus 100 and the estimation apparatus 300. As for the wired communication described above, any known wired communication technique may be used. Similarly, as for the wireless communication described above, any known wireless communication technique may be used. For example, in the wireless communication, a wireless LAN such as that based on Wi-Fi (registered trademark) may be used, or a short distance communication system such as near field communication (NFC), Bluetooth (registered trademark), ZigBee (registered trademark), or the like may be used.

In the present embodiment, the sensor 400 includes an acceleration sensor 401, a heartbeat sensor 402 a temperature sensor 403, and an angular velocity sensor 404. However, the sensor 400 may include part of the acceleration sensor 401, the heartbeat sensor 402, the temperature sensor 403 and the angular velocity sensor 404. The sensor 400 may further include another sensor such as a humidity sensor, a barometric sensor, and/or the like for detecting a state of a circumstance in which a subject is located.

The acceleration sensor 401 is worn on a subject's body part to be measured such that an acceleration at this body part can be measured. The acceleration sensor 401 may be a one-axis acceleration sensor capable of measuring an acceleration in one direction, or a two-axis acceleration sensor capable of measuring an acceleration in each of two directions perpendicular to each other, or a three-axis acceleration sensor capable of measuring an acceleration in each of three directions perpendicular to each other. Use of an acceleration sensor with two or more axes makes it possible to detect an acceleration in a desired direction regardless of the orientation of the acceleration sensor. Two or more one-axis acceleration sensors may be used to detect an acceleration in each of two or more directions. In the present embodiment, by way of example but not limitation, the acceleration sensor 401 may be worn on a foot of a subject such that an acceleration of the foot is measured in a direction in which the subject moves. More specifically, the acceleration sensor 401 measures the acceleration of the foot of the subject when the subject is spending his/her daily life or when the subject receives a motor test. The exercise in the motor test may include walking or running. The direction in which the subject moves is a direction in which the subject walks or runs. In the present embodiment, specific examples of acceleration sensor values obtained as measured values from the acceleration sensor 401 are three-axis acceleration values measured at a left ankle, a right ankle, and a waist.

The acceleration sensor 401 is worn on a foot or a waist of a subject who is exercising. More specifically, the acceleration sensor 401 is worn at a location close to an ankle of the subject. The location close to the ankle of the subject may be an ankle, instep, or a sole. FIG. 2 illustrates an example of a location at which the acceleration sensor 401 is worn on a subject. As shown in FIG. 2, the acceleration sensor 401 may be worn on at least one of ankles of a subject. For example, the acceleration sensor 401 may be attached to a band 400a worn around an ankle of a subject. Alternatively, the acceleration sensor 401 may be disposed in a shoe of a subject.

Figure 3:
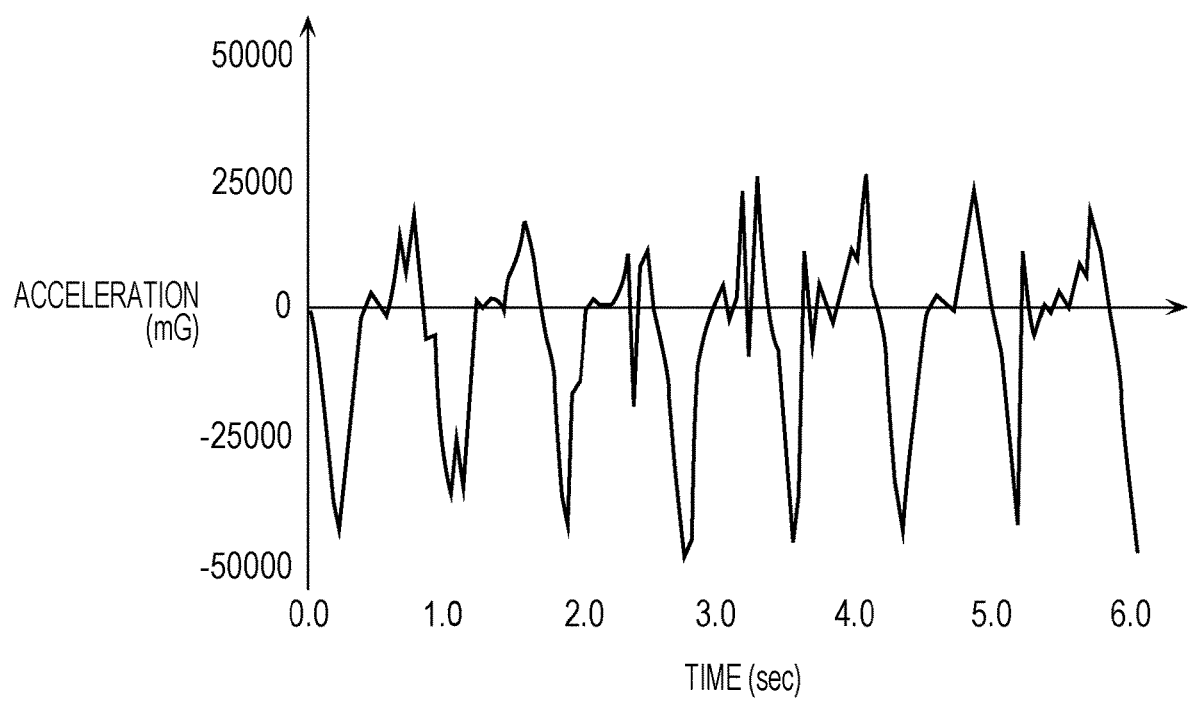
FIG. 3 is a diagram illustrating an example of a measured acceleration in a walking direction detected by an acceleration sensor worn on a right foot of a walking subject.

FIG. 3 is a graph showing an example of a result of a measurement of an acceleration of a foot of an exercising subject detected using the acceleration sensor 401. That is, in the example shown in FIG. 3, the acceleration in the moving direction of the subject walking in the motor test was measured by the acceleration sensor 401. More specifically, the 6-minute walk test was performed as the motor test, and the result of the measurement performed by the acceleration sensor 401 is shown for that obtained in a particular time segment in the 6-minute walk test. Note that in this example shown in FIG. 3, the measurement of the acceleration was measured for a period of 6 seconds. In FIG. 3, a vertical axis represents the acceleration (in units of mG) and a horizontal axis represents time (in units of sec). Note that 1 G=9.80665 m/s$^2$. In the graph shown in FIG. 3, a positive direction of the acceleration is defined in a direction in which the subject moves forward.

The heartbeat sensor 402 measures a heart rate of a subject. The heartbeat sensor 402, measures the heart rate of the subject when the subject is spending his/her daily life or when the subject is receiving a motor test. The heartbeat sensor 402 may be disposed, for example, on a wrist, an ankle, or a chest of the subject.

The temperature sensor 403 measures a body temperature of a subject. The temperature sensor 403 measures the body temperature of the subject when the subject is spending his/her daily life or when the subject is receiving a motor test. The temperature sensor 403 may be disposed at a location close to the location of the acceleration sensor 401 or the heartbeat sensor 402, or at a location apart from the location of the acceleration sensor 401 or the heartbeat sensor 402.

The angular velocity sensor 404 measures an angular velocity of a subject. The angular velocity sensor 404 measures the angular velocity of the subject when the subject is spending his/her daily life or when the subject is receiving a motor test. The angular velocity sensor 404 may be disposed at a location close to the location of the acceleration sensor 401 or at a location apart from the location of the acceleration sensor 401. Specific examples of angular velocity sensor values measured by the angular velocity sensor are three-axis angular velocity values at a left ankle, a right ankle, a waist, or the like. Estimation information generation apparatus 100

The data acquirer 110 acquires at least one or more sets of learning data wherein each set includes an action sensor value and a motor ability value in a predetermined time period. The action sensor values include a result of measurement performed by the sensor 400 or the like over the predetermined time period. More specifically, the action sensor values include measured values that are associated with measurement times. Associating of measured values with measurement times may be performed, for example, by the sensor 400 or the data acquirer 110 each time a measured value is acquired, or may be performed by another constituent element of the data acquirer 110 in the estimation information generation apparatus 100. The measured value may be a measured value directly acquired from the sensor 400 or a measured value stored in a storage unit such as the first storage 200.

The motor ability value is an ability value in terms of a muscle strength, endurance, a balancing ability, or the like, corresponding to an action sensor value. Examples of motor ability values include a muscle strength value, a maximum oxygen intake, a balancing ability value, etc., as described in further detail below. The action sensor value and the motor ability value may be prepared to implement estimation knowledge of the estimation information generation apparatus 100. The action sensor value and the motor ability value may be specific information related to a specific subject or may be general information applicable to many unspecified subjects. A combination of an action sensor value and a motor ability value may be a combination of an action sensor value acquired during a motor test or the like from a subject via the sensor 400 and a motor ability value detected from the subject via various kinds of apparatus. That is, as for the action sensor value and the motor ability value, not estimated values but actually measured values may be employed. The data acquirer 110 acquires a set of an action sensor value and a motor ability value for use as learning data in the estimation information generation apparatus 100.

The initial feature determiner 120 determines a specific time segment, which is a time segment in which motor ability is estimated in learning, and a feature to be extracted in the specific time segment, by selecting from action sensor values acquired by the data acquirer 110. More specifically, the initial feature determiner 120 determines the feature to be extracted in the specific time segment and calculates a numeric value indicating the feature value. The initial feature determiner 120 then employs the calculated feature value as an initial value of the feature value for the extracted feature. Note that the predetermined time period, that is, the measurement period of the action sensor value, is divided into a plurality of pieces of time periods referred to as time segments. Note that the feature is a feature of a measurement parameter of the sensor 400. For example, the feature may be an index of a measured value of the parameter, such as a mean value, a variance, an entropy, a correlation coefficient, a PCA (Principal Component Analysis), a RBM (Restricted Boltzmann Machine) or the like. The feature value may be a numeric value calculated, using the index, from the measured values of the parameter acquired in the time segment. Note that the initial feature determiner 120 may calculate feature values of a plurality of features.

For example, in a case where the feature to be extracted is a feature of an acceleration, that is, the index, the initial feature determiner 120 may determine a specific time segment and a feature to be extracted for the acceleration according to a predetermined method, calculate a feature value of the extracted feature of the acceleration from measured values of the acceleration in the specific time segment, and employ the calculated feature value as the initial value of the feature value. Alternatively, the initial feature determiner 120 may arbitrarily determine the specific time segment and the feature to be extracted for the acceleration, calculate a feature value of the extracted feature of the acceleration from measured values of the acceleration in the specific time segment, and employ the calculated feature value as the initial value of the feature value. Alternatively, the initial feature determiner 120 may use a preset specific time segment and a preset initial value for a feature value of an extracted feature. Preferably, the time segment may have a length during which a feature value does not have two or more different behaviors. More specifically, for example, the time segment may preferably have a length in which two or more different actions occur as actions indicated by measured values. In other words, preferably, the time segment may have a length in which no change occurs in tendency of measured values. As described later, the time segment length may be equal to several seconds or several ten seconds, and more specifically, 1 second, 5 seconds, 10 seconds, 15 seconds, 20 seconds, 25 seconds, 30 seconds, or the like.

From the action sensor value acquired by the data acquirer 110, the initial feature calculator 130 calculates a feature vector corresponding to the specific time segment and the feature value of the extracted feature determined by the initial feature determiner 120. More specifically, the feature vector calculated by the initial feature calculator 130 includes, as its element, the feature value calculated, for the extracted feature, from the measured value of the action sensor value included in the specific time segment. The feature vector may include two or more elements indicating feature values of two or more respective extracted features.

The weight adjuster 140 adjusts a weight vector according to an estimation equation including the feature vector calculated by the initial feature calculator 130 and the feature vector such that it is possible to estimate the motor ability value acquired by the data acquirer 110. The weight vector is a vector that defines weights assigned to respective elements of the feature vector. In the above-described estimation equation used in estimating the motor ability value from the feature vector, the respective elements of the feature vector are weighted according to the weight vector in the estimation calculation process such that a proper motor ability value is obtained as a result.

The feature gradient calculator 150 determines a gradient with respect to the feature vector from the motor ability value acquired by the data acquirer 110, the feature vector calculated by the initial feature calculator 130, and the weight vector calculated by the weight adjuster 140. The gradient with respect to the feature vector may be, for example, a gradient of elements with respect an error of the estimation equation of the feature vector. Note that the gradient is a vector, and hereinafter the gradient will also be referred to as the feature gradient vector. The feature gradient vector may be given, for example, by differentiating partially the error of the estimation equation with respect to the feature vector. Further details of the feature gradient vector will be described later.

The feature candidate calculator 160 determines a candidate for a new time segment by employing a time segment different from the time segment used in calculating the current feature vector, that is, a time segment different from the specific time segment, as the candidate for the new time segment. For example, the feature candidate calculator 160 may determine a plurality of new time segments as candidates. Each of the new time segments may be arbitrarily selected within the measurement period of the action sensor value as long as the time segments are different from the specific time segment which is the time segment corresponding to the current feature vector. The feature candidate calculator 160 determines a new time segment for the feature corresponding to the feature value included in the current feature vector such that the new time segment is different from the specific time segment, and then the feature candidate calculator 160 calculates a feature value of the feature using measured values included in the determined time segment. The feature candidate calculator 160 then calculates a feature candidate vector so as to include the calculated feature value as its element. Note that the number of feature candidate vectors is the same as the number of time segments determined as candidates. Further details of the feature candidate vector will be described later.

The feature seeker 170 seeks, from a plurality of feature candidate vectors calculated by the feature candidate calculator 160, a feature candidate vector whose difference from the current feature vector has a highest degree of coincidence with the feature gradient vector. More specifically, the feature seeker 170 seeks such a feature candidate vector that satisfies a condition that signs of elements of a difference vector indicating a difference between the current feature vector and the feature candidate vector have a highest degree of coincidence with signs of elements of the feature gradient vector. Note that in the present embodiment, as will be described later, the difference is given, by way of example, the difference obtained by subtracting the feature candidate vector from the current feature vector, but the difference is not limited to that.

The judger 180 determines whether learning is to be ended or not based on a result of seeking of the feature candidate vector performed by the feature seeker 170. More specifically, in a case where a feature candidate vector has been extracted in the seeking by the feature seeker 170, the judger 180 determines that learning of the weight vector, that is, the adjustment is to be continued using the extracted feature candidate vector as a new feature vector. In a case where no feature candidate vector is extracted in the seeking of the feature candidate vector, the judger 180 determines that the learning is completed. In this case, existing information such as the existing weight vector or the like is employed as a proper constituent element of the estimation knowledge for the motor ability value. Note that the weight adjuster 140, the feature gradient calculator 150, the feature candidate calculator 160, the feature seeker 170, and the judger 180 form a learning unit that makes the estimation knowledge for the motor ability value perform machine learning, and more specifically makes the estimation knowledge for the motor ability value learn the weighting in the estimation process.

The estimation knowledge outputter 190 stores, in the first storage 200, the new time segment corresponding to the feature candidate vector determined by the feature seeker 170 together with the feature corresponding to the feature value included in the feature candidate vector, that is, the estimation knowledge outputter 190 stores the combination of the new time segment and the feature in the first storage 200, while the estimation knowledge outputter 190 stores the weight vector calculated by the weight adjuster 140 in the second storage 210. First storage 200 and second storage 210

The first storage 200 and the second storage 210 are configured to be capable of storing various kinds of information and reading the stored information. More specifically, the first storage 200 stores information as to a combination of a time segment and a feature extracted from an action sensor value. The first storage 200 may store the action sensor value. In this case, the first storage 200 may store only the measured value of the action sensor value or the combination of the measured value of the action sensor value and the corresponding measurement time. The second storage 210 stores estimation knowledge structure information such as a weight vector or the like. The first storage 200 and the second storage 210 each may be realized using a hard disk or a semiconductor memory. The first storage 200 and the second storage 210 may be realized as separate elements or may be integrated in a single element. Estimation apparatus 300

The estimation apparatus 300 estimates a motor ability value from an input action sensor value using the estimation knowledge generated by the estimation information generation apparatus 100. For example, when a result of measurement on an exercising subject is input from the sensor 400, the estimation apparatus 300 estimates a motor ability value of the exercise corresponding to an input parameter.

The sensor value acquirer 310 acquires action sensor values including measurement results over a predetermined time period from one or more sensors 400 worn on corresponding one or more predetermined parts of a subject.

To extract a feature for use in estimating a motor function from the action sensor values, the feature acquirer 320 extracts a combination of a time segment and a feature to be extracted from the action sensor value from the first storage 200. As described above, the combination is a combination of a time segment and a feature effective in the motor function estimation, wherein the time segment and the feature are calculated by the estimation information generation apparatus 100. More specifically, the combination is a combination of a time segment and a feature stored in the first storage 200 by the estimation knowledge outputter 190 wherein the time segment corresponds to a feature candidate vector and the feature corresponds to feature values included in the feature candidate vector.

The feature value calculator 330 calculates, from the action sensor values acquired by the sensor value acquirer 310, a feature vector corresponding to the time segment and the feature acquired by the feature acquirer 320. More specifically, the feature value calculator 330 extracts a time segment corresponding to the acquired time segment from the time segments associated with the action sensor values. The feature value calculator 330 then calculates a feature value of the acquired feature using the measured values included in the extracted time segment. For example, in a case where there are a plurality of features corresponding to the extracted time segment, the feature value calculator 330 calculates a plurality of sets of feature values. The feature value calculator 330 then calculates a feature vector using the extracted time segment and the calculated feature value.

The estimation knowledge acquirer 340 acquires, from the second storage 210, a weight vector as estimation knowledge for use in estimating a motor ability value from the feature vector.

The motor function estimator 350 estimates the motor ability value using the feature vector calculated by the feature value calculator 330 and the weight vector acquired by the estimation knowledge acquirer 340. For example, the motor function estimator 350 estimates the motor ability value of the subject using the weight vector and the feature vector according to the estimation equation used, by the weight adjuster 140, in the adjustment of the weight vector.

The outputter 360 outputs the motor ability value estimated by the motor function estimator 350. The outputter 360 may output the motor ability value to the display 500 or an external apparatus different from the motor function estimation system 1000.
Display 500

Figure 4:
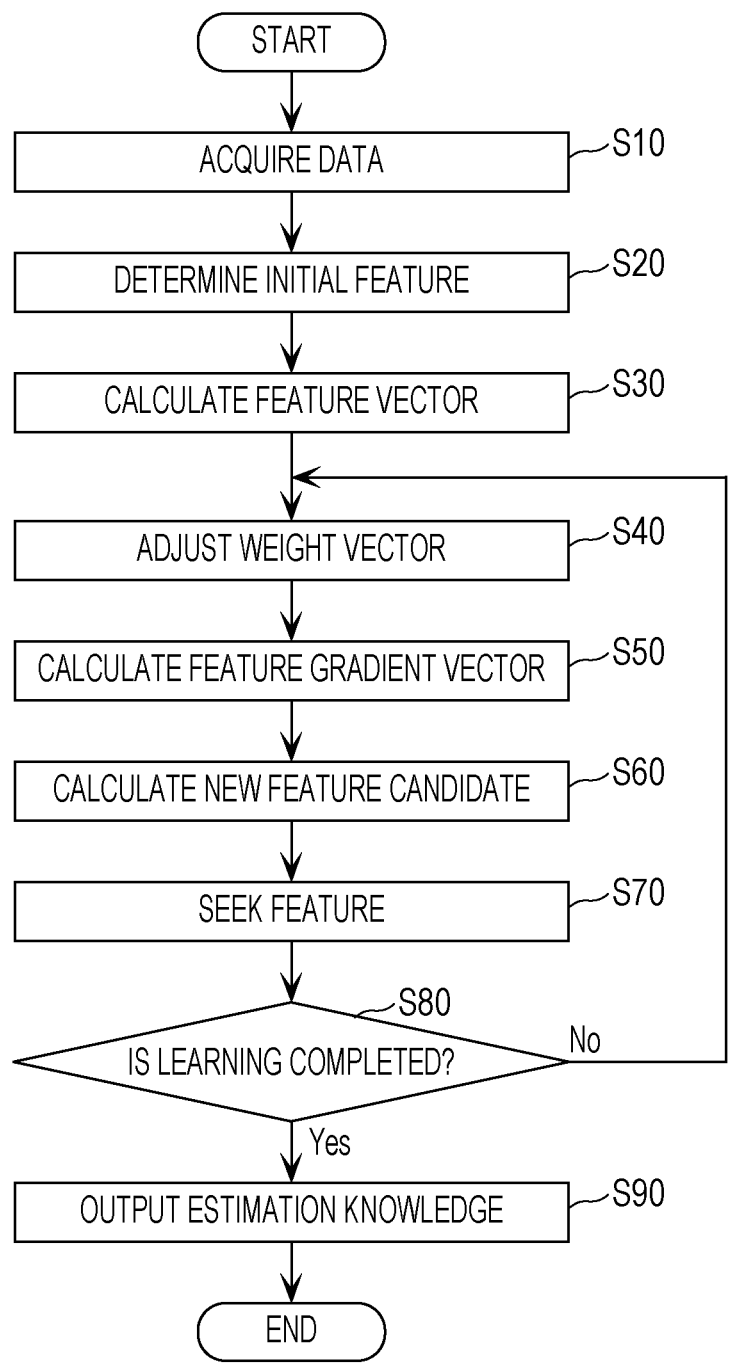
FIG. 4 is a flow chart illustrating an example of a flow of an operation of generating estimation knowledge in a motor function estimation system according to an embodiment.

The display 500, which is also called a notification unit, outputs visually and/or audibly various kinds of information provided by the estimation apparatus 300. More specifically, the display 500 provides the information about the motor ability value estimated by the estimation apparatus 300. For example, the display 500 may be a display or a speaker. For example, the display 500 may be a display including a display panel such as a liquid crystal panel, an organic or inorganic EL (Electro Luminescence) panel, or the like, a speaker, or a combination thereof. The display 500 may be a part of a computer apparatus including the motor function estimation system 1000, or may be a part of an apparatus such as a computer apparatus or the like that does not include the motor function estimation system 1000. The display 500 may be a part of a portable terminal of a subject such as a smartphone, a smart watch, a tablet, or the like. Alternatively, the display 500 may be disposed, together with the sensor 400, on the band 400a shown in FIG. 2.
2. Operation of Motor Function Estimation System According to Embodiments Next, an operation of the motor function estimation system 1000 according to an embodiment is described below. More specifically, an operation of the estimation information generation apparatus 100 and an operation of the estimation apparatus 300 are mainly described.
2-1. Estimation Information Generation Process by Estimation Information Generation Apparatus Referring to FIG. 4, a processing operation of generating estimation information by the estimation information generation apparatus 100 is described below. FIG. 4 is a flow chart illustrating an example of a flow of an operation of generating estimation information by the motor function estimation system 1000 according to an embodiment.

Step S10: The data acquirer 110 acquires a motor ability value of a subject and an action sensor value of the subject. Note that the action sensor value of the subject includes a set of a measured value provided by the sensor 400 worn on the subject and a measurement time corresponding to the measured value, that is, the time at which the measured value was measured. In this embodiment, the acquired motor ability value and the action sensor value are not estimated values but values actually measured for a subject. The action sensor value includes data acquired over a predetermined time period. As described above, the action sensor value is information including a set of data and a measurement time corresponding to the data. An example of data includes acceleration values over a particular time period as shown in FIG. 3. The motor ability value of a subject is, for example, a muscle strength value such as a lower extremity muscle strength, a maximum oxygen intake, a balancing ability value and/or the like.

The lower extremity muscle strength is, for example, given by a mean value of knee extension muscle strength. For example, the lower extremity muscle strength may be measured such that a knee joint is bent and extended while controlling the angular velocity thereof to be constant, and a muscle strength or a joint torque that occurs in the bending and extending is measured. This method is called an isokinetic strength measurement method. The balancing ability is, for example, the ability of a subject to keep his/her balance against a gravitational force. More specifically, the balancing ability is the ability of a subject to keep his/her balance by keeping the center of gravity of his/her body within a base of support. The balancing ability is also the ability of getting back the center of gravity of the body into the base of support when the center of gravity of the body is goes out from the base of support. The balancing ability value may be measured using a functional reach test in which the maximum distance by which an arm can be extended is measured, or using a standing on one leg with eyes closed or open test in which a time for which a subject can keep standing with his/her one leg with eyes closed or open is measured, or other similar methods. The maximum oxygen intake is an example of an index indicating an endurance. The maximum oxygen intake may be detected by measuring a breathing quantity, an oxygen consumption, and a carbon dioxide emission of a subject when a load imposed on the subject is increased stepwise using a treadmill or a bicycle ergometer.

For example, the data acquirer 110 may acquire action sensor values and motor ability values of a subject from a database. In the database, data may be stored, for example, such that a subject ID and a corresponding action sensor value and motor ability value are associated with each other and stored as a set. Alternatively, the data acquirer 110 may acquire action sensor values from the sensor 400 and acquire motor ability values from a database. The data acquirer 110 may refer to a subject ID associated with an action sensor value and may acquire a motor ability value corresponding to the subject ID from a database.

In other words, the data acquirer 110 acquires, as learning data for learning generating motor function estimation knowledge, a plurality of pieces of data each including a set of an action sensor value and a motor ability value measured by a predetermined time period by the sensor 400. Note that the action sensor values and the motor ability values may be given by measured values for a specific subject or by measured values for many unspecific subjects. By using action sensor values and motor ability values given by measured values measured for a specific subject, it is possible to obtain estimation knowledge for the specific subject. By using action sensor values and motor ability values given by measured values measured for many unspecific subjects, it is possible to obtain general estimation knowledge.

Step S20: Based on action sensor values, and more specifically, for example, based on parameters of measured values included in the action sensor values, the initial feature determiner 120 determines a plurality of features to be extracted and further determines a time segment for which feature values of the these features are to be calculated. For example, the initial feature determiner 120 includes a feature determination database and stores a plurality of pieces of selection standard data in the feature determination database. Note that the feature determination database may be stored in the first storage 200.

For example, each selection standard data may include information as to one parameter of a measured value, a feature effective for this parameter, and a time segment effective for calculating a feature value of this feature. Each selection standard data may be data indicating a set of a parameter, a future effective for the parameter, and a time segment effective for calculating a feature value of the feature. Each selection standard data may be data separately including a feature effective for a parameter and a time segment for which a feature value of the feature is to be calculated. In each selection standard data, a plurality of features may be associated with one parameter. In each selection standard data, a plurality of time segments may be associated with one feature. Each selection standard data may be a set of associated data elements including a parameter of a measured value, one or more features each effective for representing a feature of the parameter, and a time segment effective for calculating a feature value of each feature.

The initial feature determiner 120 refers to a plurality of pieces of selection standard data stored in the feature determination database, and determines a feature effective for a parameter of a measured value and a time segment for which a feature value of the feature is calculated. The time segment determined by the initial feature determiner 120 is an initial time segment, and the feature value of the feature calculated for this time segment by the initial feature determiner 120 is an initial value of the feature value. Alternatively, the initial feature determiner 120 may randomly determine a time segment and a feature in a predetermined time segment.

In a case where one piece of selection standard data includes a plurality of features, the initial feature determiner 120 randomly selects at least two features from the plurality of features, and employs the selected features as features to be extracted. Examples of features include a mean value, a variance, an entropy, a correlation coefficient, PCA (Principal Component Analysis), RBM (Restricted Boltzmann Machine), etc. The initial feature determiner 120 employs a time segment effective for the determined feature as the initial value of the time segment and employs a feature value of the feature calculated using a measured value in this time segment as the initial value of the feature value. Note that the initial feature determiner 120 determines as many initial values as there are determined features.

FIG. 5 exemplarily illustrates sets of data each including a feature and a time segment determined by the initial feature determiner 120 according to the selection standard data. In FIG. 5, each data set includes a feature to be extracted and a time segment in a case where PCA is used. In this example, in selection standard data, a feature corresponding to a parameter of a measured value included in action sensor values is a coefficient of a principal component when an action sensor value is represented using a principal component vector of PCA, and a time segment effective for the coefficient of the principal component representing the feature is a time segment from 0 to 30 sec. In this example, as a result of PCA performed on one action sensor value, coefficients of 1st to 32nd principal components are extracted as 32 features. Values of the coefficients of the respective principal components are feature values. The initial feature determiner 120 extracts 32 features and feature values thereof from each of a plurality of action sensor values acquired in step S10. The 32 features are sequentially assigned feature numbers n ($1 \leq n \leq 32$).

In the present example, the action sensor values include measured values obtained over a period of 6 minutes. In the measurement period of 6 minutes in terms of the action sensor values, the initial feature determiner 120 determines a start time tn of a time segment (with a length of 30 seconds in the present example) corresponding to a feature of a feature number n and also determines a coefficient of a principal component with a principal component number kn of PCA. Note that the principal component numbers kn are ordinal numbers of the principal components shown in FIG. 5. In the present example, the initial feature determiner 120 determines the start time tn and the number kn such that start time tn=0 and number kn=n. In this case, the features with the feature numbers 1 to 32 are respectively coefficients of the 1st to 32nd principal components of the principal component vector of PCA obtained when action sensor values in the corresponding time segment from 0 sec to 30 sec are represented by the principal component vector. Note that alternatively the initial feature determiner 120 may arbitrarily determine the start time tn and the number kn.

In PCA, when action sensor values in a certain time segment are given by A and principal component vectors including principal component elements with the same principal component numbers are respectively given by $P_1$ to $P_{32}$, A is given as $A = P_1 \cdot C_1 + P_2 \cdot C_2 + \ldots + P_{32} \cdot C_{32}$ where $C_1$ to $C_{32}$ respectively denote coefficients of the principal components with the same principal component numbers. That is, the features of the action sensor values can be represented by the coefficients $C_1$ to $C_{32}$.

Figure 6:
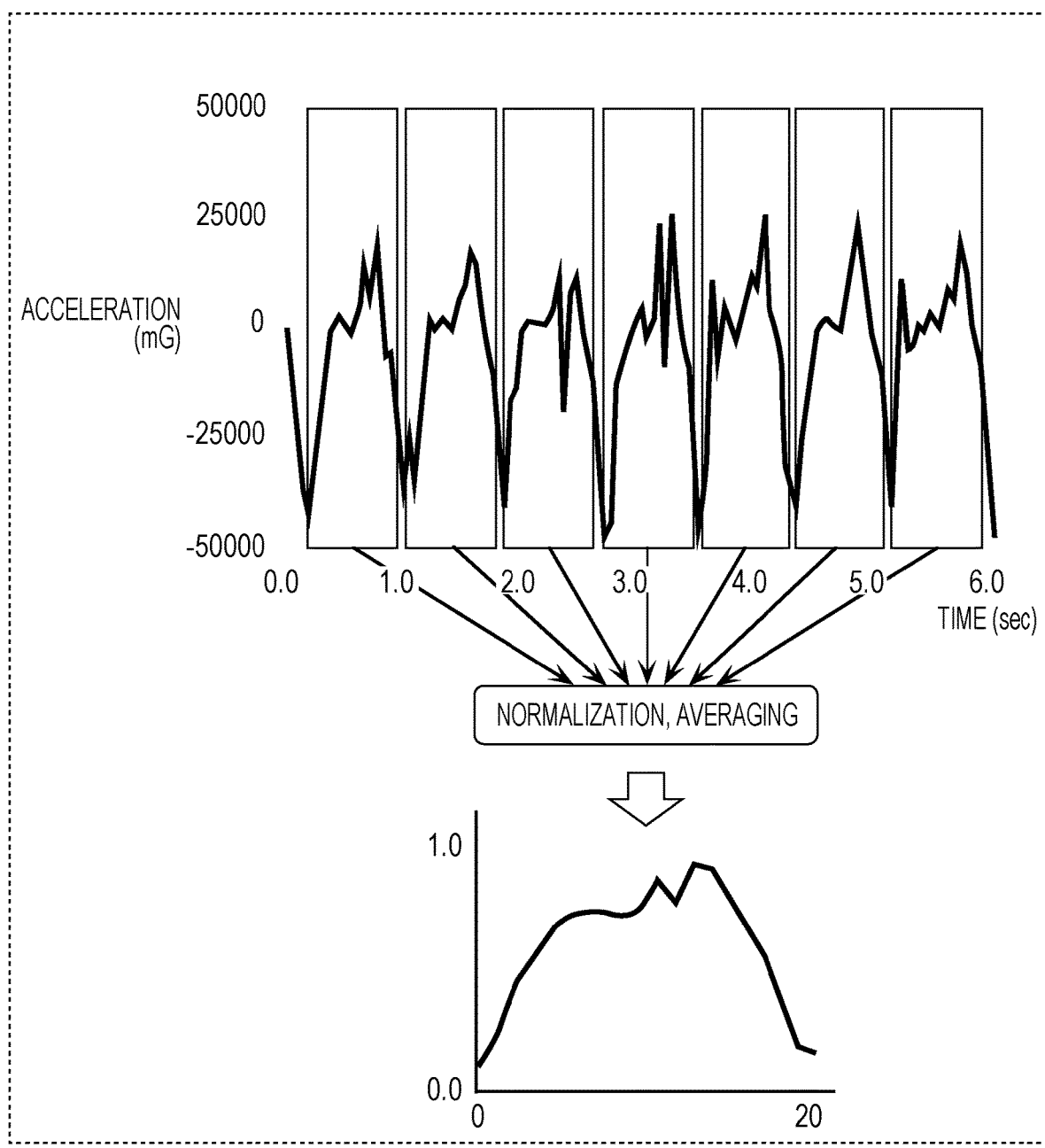
FIG. 6 is a diagram conceptually illustrating an example of a method of calculating an average walking waveform.

FIG. 6 illustrates another example of a procedure of extracting feature values according to the selection standard data. In this example, feature values and time segments are calculated for a case in which mean values are employed as features. In this example, the selection standard data includes arithmetic means of normalized action sensor values corresponding to features of parameters of measured values included in the action sensor values. The features are obtained as a result of the following calculation. The action sensor values in a time period from 0 sec to 6 sec are divided into time segments and then the action sensor values in the respective resultant time segments are normalized and the arithmetic means thereof are calculated. The time segments effective for these features each have a length of about 6/7 sec which corresponds to one walking period.

Like the example shown in FIG. 3, the data shown in FIG. 6 includes data of the acceleration in a period of 6 sec in which walking was performed. FIG. 6 conceptually illustrates an example of a method of calculating, as a feature, an average walking waveform in terms of the acceleration from an acceleration waveform for a period of 6 seconds. In the example shown in FIG. 6, from the total time period (of 6 sec), the initial feature determiner 120 extracts seven acceleration values for respective time segments (about 6/7 sec) each corresponding to one walking period. Thus, an acceleration value is extracted for each time segment of about 6/7 sec. Each acceleration value forms a walking waveform representing one step in walking. The initial feature determiner 120 normalizes each of seven walking waveforms, and determines an arithmetic mean of the normalized seven walking waveforms thereby obtaining an average acceleration that is given as an input when a feature value is calculated.

Step S30: Next, the initial feature calculator 130 calculates a feature vector using the feature values of the plurality of features determined using the action sensor values in step S20. Note that the feature values of the plurality of features determined in step S20 are referred to as the initial feature values. The feature vector produced herein includes the plurality of initial feature values as elements. For example, in the case shown in FIG. 5, the feature vector X is a coefficient vector C. The coefficient vector C may be ($C_1$, $C_2$, ..., $C_{32}$).

Step S40: Furthermore, using the calculated feature vector, the weight adjuster 140 calculates and adjusts a weight vector for use in estimating the motor ability value acquired in step S10.

The motor ability value y is estimated according to an estimation equation f(X, W) including the feature vector X and the weight vector W corresponding to the feature vector X. A specific example of an estimation method is to estimate a correct value from the feature vector and the weight vector using a known learning method such as linear regression, neural network, logistic regression, or the like.

The weight vector may be adjusted based on the error function $E = (y - f(X, W))^2$ representing the square of the estimation error of the motor ability value such that the adjusted weight vector is given as $W' = W - a \cdot \partial E / \partial W$ using the gradient of the error function with respect to the weight where W is the original weight vector and W' is the adjusted weight vector, $\partial E / \partial N$ is the gradient of the error function with respect to the weight, which is given by differentiating partially the error function with respect to the weight vector, and a is a constant. That is, in a case where the motor ability value estimated using the feature vector X and the weight vector W according to the estimation equation has an error with reference to the motor ability value acquired in step S10, the weight adjuster 140 adjusts the weight vector W using the error function with respect to the error. Note that the error function E is an example of an index indicating the error between the estimated value of the motor ability value estimated using the weight vector and the actually acquired motor ability value.

Step S50: The feature gradient calculator 150 calculates the gradient $\partial E / \partial X$ of the error function E with respect to the feature vector (this gradient will also referred to as the feature gradient vector) using the motor ability value acquired in step S10, the feature vector X calculated in step S30, and the weight vector W' adjusted in step S40. Note that in the gradient $\partial E / \partial X$, X is the feature vector. Also note that the gradient $\partial E / \partial X$ is an example of a gradient vector, with respect to the feature vector, of the index indicating the error of the estimated value of the motor ability value estimated using the weight vector from the actual motor ability value.

The feature vector X may be updated using the gradient $\partial E / \partial X$ such that $X' = X - b \cdot \partial E / \partial X$ where X' is the updated feature vector and b is a constant. As with the weight vector, if the feature vector can be changed according to the formula described above, it is possible to reduce the error between the estimated value of the motor ability value and the actually acquired motor ability value. However, the feature values are elements of the feature vector and are calculated from the action sensor values, and thus, unlike the weight vector, it is not possible to directly change the feature values. Therefore, the time segment for which the feature vector is calculated is changed, and a feature vector is generated such that the elements of the feature vector are given by the feature values calculated for the changed time segment thereby obtaining the changed feature vector. When the feature vector is changed in the above-described manner, the feature vector is changed in a direction of the gradient $\partial E / \partial X$ in which a reduction in the error described above occurs. Note that in the conventional machine learning, only the weight vector is learned and changed to obtain a better result. In contrast, in the estimation information generation apparatus 100, by performing the process described above, it is possible to both adjust the weight vector so as to improve the estimation accuracy and seek the feature vector in step S70 as described later. This cannot be achieved in the conventional machine learning. This capability of achieving the adjustment of the weight vector and the seeking of the feature vector is useful in performing estimation, in particular, in a situation in which sensor data is input for a long period without preliminary knowledge as to what feature is useful.

Step S60: The feature candidate calculator 160 calculates a feature candidate vector using a new time segment and a new feature corresponding to the new time segment. The new time segment and the new feature are respectively a time segment and a feature at least one of which is different from the time segment or the feature determined by the initial feature determiner 120. More specifically, the feature candidate calculator 160 determines a new time segment for which at least one feature is to be changed, and calculates a feature value of this feature using action sensor values in the determined time segment. The feature candidate calculator 160 then employs, as a feature candidate vector, a new feature vector including the calculated feature value as its element. Note that the feature candidate calculator 160 may arbitrary determine the new time segment.

For example, in the case shown in FIG. 5, the feature candidate calculator 160 determines a candidate for the new time segment using the features with the feature numbers n ($1 \leq n \leq 32$). For example, as the candidate for the new time segment, the feature candidate calculator 160 may employ time segments obtained by shifting, by a fixed amount, the current start time tn and the end time tn+30 of the feature number n. For example, in a case where the current start time tn of the feature number n is shifted by 15 sec, candidates for the new time segments are obtained as follows: a time segment from tn−30 to tn, a time segment from tn−15 to tn+15, a time segment from tn to tn+30, a time segment from tn+15 to tn+45, a time segment from tn+30 to tn+60, and so on.

The feature candidate calculator 160 performs PCA analysis on action sensor values in time segments corresponding to the respective candidates for the new time segments. The feature candidate calculator 160 then calculates coefficients of 1st to 32nd principal components of a PCA principal component vector representing a plurality of action sensor values in the new time segments. When there are M candidates for new time segments, a calculation is performed to determine coefficients of feature numbers n, that is, M×32 values as new candidate values for feature values. More specifically, the feature values of the features of the feature numbers n each can take one of coefficients of the 1st to 32nd principal components, that is, one of 32 coefficients. Furthermore, 32 feature values of the feature numbers n are calculated for M new time segments. As a result, M×32 values are calculated as new candidate values for feature values. The feature candidate calculator 160 generates a feature candidate vector corresponding to the feature number n by arranging the values of the above-described coefficients, that is, the feature values calculated for all action sensor values acquired by the data acquirer 110. Because there are M×32 new candidate values for the feature values, M×32 feature candidate vectors are obtained. In a case where N action sensor values are acquired by the data acquirer 110, each feature candidate vector includes N elements. The feature candidate calculator 160 calculates the feature candidate vectors in the above-described manner for all feature numbers (1 to 32 in the present example).

Step S70: The feature seeker 170 seeks, from the plurality of feature candidate vectors calculated in step 360, a feature candidate vector most suitable for moving the current feature vector in the direction of the feature gradient vector. The feature seeker 170 seeks a feature candidate vector that satisfies a predetermined condition based on the feature gradient vector. More specifically, in a case where the feature seeker 170 seeks a feature candidate vector of an n-th feature, the feature seeker 170 uses an N-dimensional vector (feature vector) whose elements are feature values, that is, values of the n-th coefficients obtained when PCA analysis is performed on the N respective action sensor values acquired by the data acquirer 110. Thereafter, the feature seeker 170 determines the degree of coincidence of signs of respective elements of a difference vector obtained as a result of subtracting the feature vector from the feature candidate vector with respect to signs of corresponding elements of the feature gradient vector, and the feature seeker 170 selects a feature candidate vector that results in the highest degree in terms of the above described coincidence.

The feature seeker 170 then updates the feature values of the current feature vector and the time segment by replacing them with the feature values of the selected feature candidate vector and the time segment corresponding to the feature values. In a case where the number of elements with the signs equal for both the difference vector and the feature candidate vector is smaller than the number of elements with the signal different between the difference vector and the feature candidate vector, the feature seeker 170 determines that no feature value to be employed in the updating is found, that is, no feature candidate vector is found. In this case, the updating is not performed. The feature seeker 170 performs the process described above for all feature numbers (1 to 32 in the present example). Thus, the feature seeker 170 updates the feature values of the current feature vector and the time segment for each of the features of the feature numbers 1 to 32 using the feature values of the selected feature candidate vector and the time segment corresponding to the feature values.

FIG. 7 illustrates an example in which the time segments and the feature values shown in FIG. 5 are updated to new time segments and feature values by the feature seeker 170. For example, in the feature of the feature number 1, the coefficient of the first principal component is maintained without being changed via the updating. The time segment is not changed for the feature of the feature number 1. In the feature of the feature number 2, the coefficient is changed from the coefficient of the second principal component to the coefficient of the fifth principal component. In the feature of the feature number 2, the time segment is shifted by 15 sec such that the time segment is changed from the time segment from 0 to 30 sec to the time segment from 15 sec to 45 sec.

As described above, the difference between each of the feature candidate vectors and the feature vector is determined by subtracting the feature candidate vector of interest from the feature vector, and a feature candidate vector is selected that results in a highest degree of coincidence between the determined difference and the feature gradient vector. In other words, a feature candidate vector satisfying the predetermined condition associated with the gradient vector is determined based on the difference between the feature candidate vector and the feature vector. Note that the weight vector is adjusted based on the determined feature candidate vector as described later, and use of the weight vector adjusted in the above-described manner based on the feature candidate vector makes it possible to achieve a greater reduction in the estimation error of the motor ability value than is achieved by using the weight vector based on the original feature vector without being changed to the feature candidate vector.

Step S80: The judger 180 determines whether the learning for motor function estimation knowledge generation is to be ended. More specifically, the judger 180 determines whether the feature value has been updated in step S70, and if it is determined that updating has been performed (No in step S80), the judger 180 determines that the learning is not yet completed. In this case, the processing flow returns to step S40. In this case, the estimation information generation apparatus 100 readjusts the weight vector using the updated feature value and the time segment. In a case where updating of the feature value is not performed in step S70 (Yes in step S80), the judger 180 determines that the learning is complete. In this case, the processing flow proceeds to step S90. Note that the judger 180 may determine whether the learning is complete by determining whether the judgement step S80 has been performed a greater number of times than a predetermined number of times. Also in a case where the process in step S70 cannot find a feature candidate vector that results in a change of the feature vector in the direction of the feature gradient vector, the judger 180 may determine that the learning is completed.

Step S90: The estimation knowledge outputter 190 stores, in the first storage 200, the new feature vector, that is, the new time segment and the new feature value calculated in step S70. More specifically, the estimation knowledge outputter 190 stores, in the first storage 200, the feature corresponding to the new feature value to indicate what feature the new feature value corresponds to. In the case shown in FIG. 7, for example, in the 2nd feature, the time segment from 15 sec to 45 sec and the coefficient of the 5th principal component are combined and stored as one set. In this storing process by the estimation knowledge outputter 190, parameters of measured values of action sensor values used in calculating the new time segment and the new feature value may also be stored together with the new time segment and the new feature. Furthermore, the estimation knowledge outputter 190 stores the weight vector acquired by the weight adjuster 140 in the second storage 210. Note that this weight vector is the newest weight vector updated in step S40. This weight vector may be associated with the new time segment and the feature described above. In a case where this newest weight vector is the only weight vector stored in the second storage 210, it does not necessarily need to associate the weight vector with the new time segment and the feature.

Via the above-described process from step S10 to step S90, the estimation information generation apparatus 100 obtains estimation knowledge including the time segment, the feature, and the weight vector necessary in estimating the motor function from action sensor values measured for a particular time.

Figure 8:
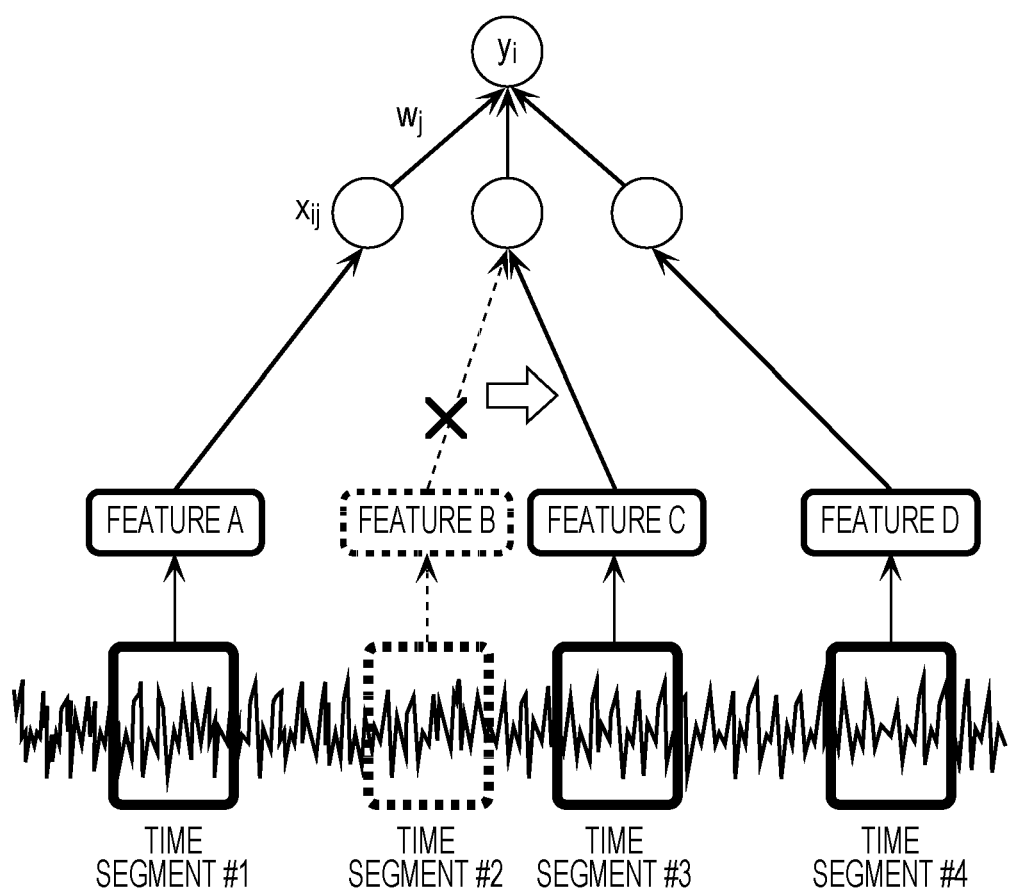
FIG. 8 is a diagram conceptually illustrating an example of an estimation method of estimation knowledge according to an embodiment.

Thus, as conceptually shown in FIG. 8, it is possible to achieve learning in terms of extraction of features and time segments from action sensor values acquired in a long time period. In FIG. 8 which conceptually shows an example of an estimation method using estimation knowledge, a motor ability value $y_i$ of a person i is estimated from given time segments and feature values calculated from the time segments. In the example shown in FIG. 8, input feature values are denoted by a feature vector $X_i$, and processes between nodes are weighted by a weight vector W. For example, in FIG. 8, in the case of machine learning in which only the weight vector is updated, if the time segment for which the feature is extracted and the feature calculated in this time segment are determined in advance, it is not allowed to change them. In the conventional machine learning, for example, when time segments #1, #2, and #4 in FIG. 8 are selected, and features A, C, and D are calculated respectively for the time segments #1, #2, and #4, these time segments and features are fixed over the entire learning process. In contrast, in the technique according to the present embodiment, it is possible to performing learning while updating the time segment and the feature so as to be more suitable for estimation of the motor ability value. In the example shown in FIG. 8, the time segment #2 and the feature B calculated from the time segment #2 are changed to the time segment #3 and the feature C.

The technique according to the present embodiment provides an advantageous effect that unlike the conventional machine learning in which when data with a huge number of dimensions is directly input, the number of parameters to be learned per data is too large, which results in a reduction in estimation accuracy and recognition accuracy, and thus it is necessary to extract features heuristically, the technique of building estimation knowledge according to the present embodiment allows it to seek a feature vector that changes in the direction of the feature gradient vector and simultaneously adjust the weight vector, and thus it is possible to effectively perform learning, without preliminary knowledge, even when given data has a huge number of dimensions as is the case with sensor data measured over a long time period. Note that the weight vector learning part may be realized using a multilayer neural network such as that shown in FIG. 9.

Figure 9:
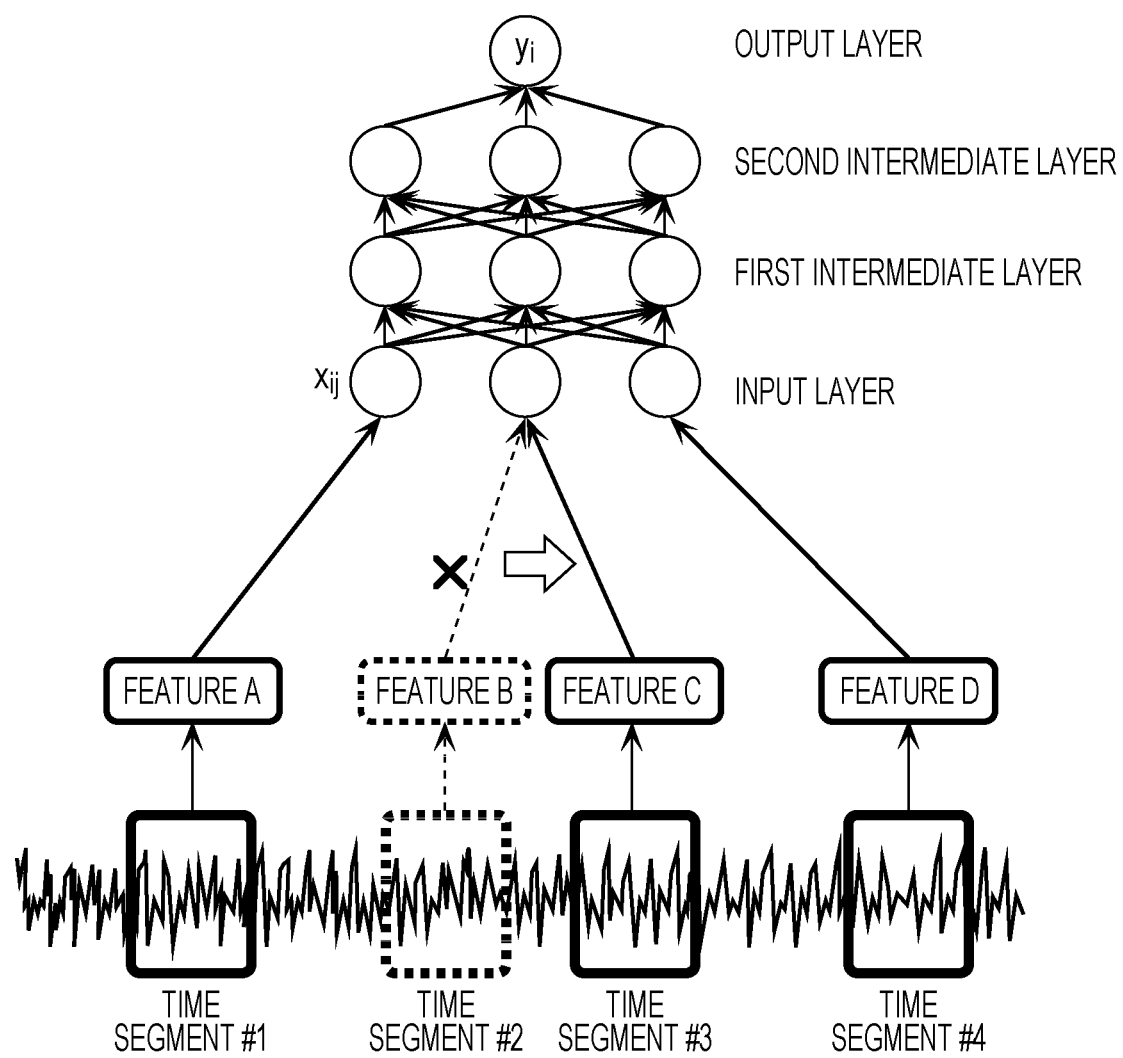
FIG. 9 is a diagram conceptually illustrating an estimation method of estimation knowledge using a neural network according to an embodiment.

In FIG. 9, a neural network is shown as an example of a machine learning unit. In general, neural networks provide information processing models simulating a cranial nerve system. The neural network has a plurality of node layers including an input layer and an output layer. Each node layer has one or more nodes. Model information of the neural network indicates the number of node layers forming the neural network, the number of nodes of each node layer, the type of the total neural network or the type of each node layer. For example, the neural network includes an input layer, intermediate layers, and an output layer. When information is input to a node of the input layer, the neural network sequentially performs a process of outputting from the input layer to a first intermediate layer, a process in the first intermediate layer, a process of outputting from the first intermediate layer to a second intermediate layer, a process in the second intermediate layer, a process of outputting from the second intermediate layer to the output layer, and a process in the output layer, and the neural network outputs an output result corresponding to the input information. Note that each node of one layer is connected to nodes of a next layer, while the connection between nodes is weighted. Information associated with nodes of one layer is weighted in connection to nodes and output to nodes of a next layer. Weight elements form a weight vector W. In the learning in the neural network, when a time segment and feature values to be calculated for this time segment, that is, a feature vector $X_i$ corresponding to the time segment are input to the input layer, node-to-node weights are adjusted such that a proper motor function value yi is output from the output layer.

2-2. Motor Function Estimation Process by Estimation Apparatus

Figure 10:
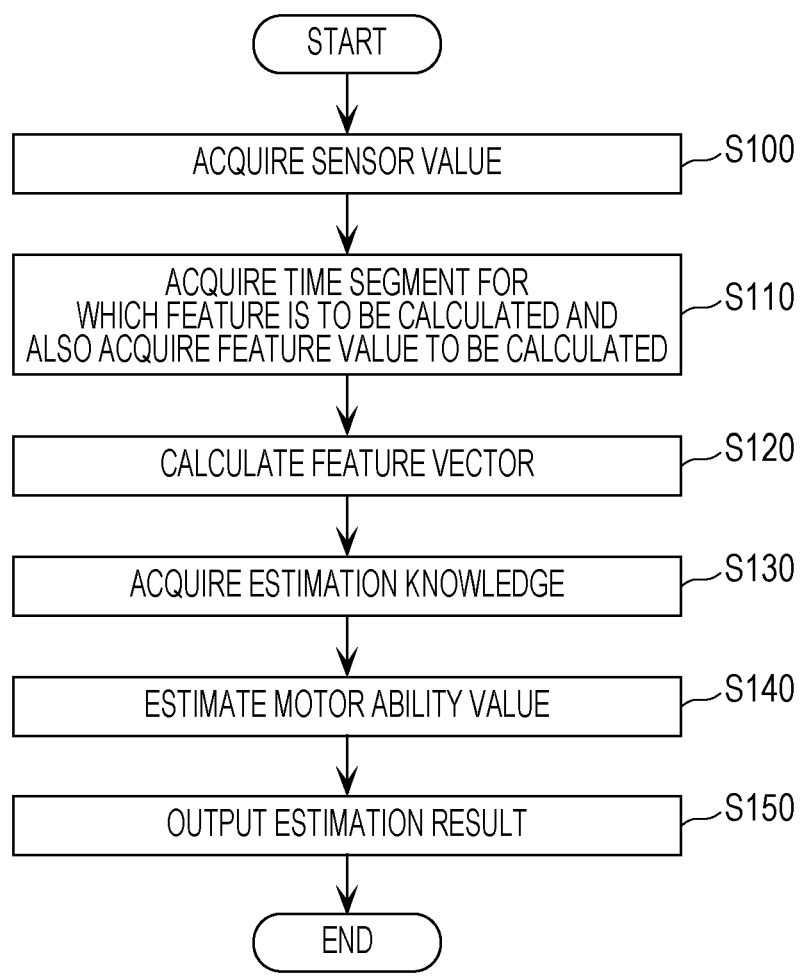
FIG. 10 is a flow chart illustrating an example of a flow of an operation of estimating a motor function in a motor function estimation system according to an embodiment.

Referring to FIG. 1 and FIG. 10, a processing operation of estimating a motor function by the estimation apparatus 300 is described below. FIG. 10 is a flow chart illustrating an example of a flow of an operation of motor function estimation performed by the motor function estimation system 1000 according to an embodiment.

Step S100: The sensor value acquirer 310 acquires action sensor values measured over a predetermined time period by the sensor 400 worn on a subject. The action sensor values include measured values in terms of an acceleration, a heart rate, a body temperature, an angular velocity, and/or the like and measurement times of the respective measured values.

Step S110: To extract feature values for use in motor function estimation from action sensor values, the feature acquirer 320 acquires, from the first storage 200, a combination of a time segment and a feature to be extracted from the action sensor values. Note that the combination of the time segment and the feature to be acquired is a combination that is stored in the first storage 200 in step S90 of the estimation information generation process. The feature acquirer 320 acquires a time segment and a feature corresponding to parameters of measured values of the action sensor values.

Step 3120: From the action sensor values acquired in step S100, the feature value calculator 330 extracts a time segment corresponding to the time segment acquired in step S110. Furthermore, from the measurement result in the extracted time segment, the feature value calculator 330 then calculates a feature value of the feature acquired in step S110. The feature value calculator 330 then calculates a feature vector whose elements are given by the calculated feature value.

Step S130: The estimation knowledge acquirer 340 acquires, from the second storage 210, a weight vector that associates the feature vector to the motor ability value. Note that the acquired weight vector is a weight vector that is stored in the second storage 210 in step S90 of the estimation information generation process. In a case where the second storage 210 includes a plurality of weight vectors stored therein, the estimation knowledge acquirer 340 may determine a weight vector to be acquired based on the correspondence to the combination of the feature and the time segment acquired in step S110. Thus, the estimation knowledge acquirer 340 acquires estimation knowledge for use in calculating a motor ability value of a motor function.

Step S140: The motor function estimator 350 estimates the motor ability value from the feature vector calculated in step S120 and the weight vector acquired in step S130. In the estimation, estimation knowledge implemented by the weight vector is used. Furthermore, the estimation uses the same estimation method as that used in the machine learning process performed by the estimation information generation apparatus 100. As for the estimation method, the estimation method illustrated by way of example in FIG. 8 may be used, or the neural network illustrated by way of example in FIG. 9 may be used. By inputting the feature vector to the estimation knowledge built using the weight vector, it is possible to output an estimated value of the motor ability. The motor function estimator 350 outputs the estimated motor ability value to the outputter 360.

Step S150: The outputter 360 outputs the motor ability value estimated in step S140. The destination of the output may be the display 500, which may directly display the motor ability value. The destination of the output may be a storage medium such as a memory or the like, which may store the motor ability value.

In the above-described process from step S110 to step S150, the time segment and the feature useful for the estimation are used, and thus it is possible to achieve high accuracy in the estimation of the motor ability value from the action sensor value for the predetermined time period even in a case where the predetermined time period is long.

EXAMPLES

Examples according to the embodiment are described below. The motor function was estimated by the motor function estimation system 1000 using the estimation method according to the embodiment, and results thereof were evaluated in comparison with estimation results according to other methods.

Figures 11, 12:
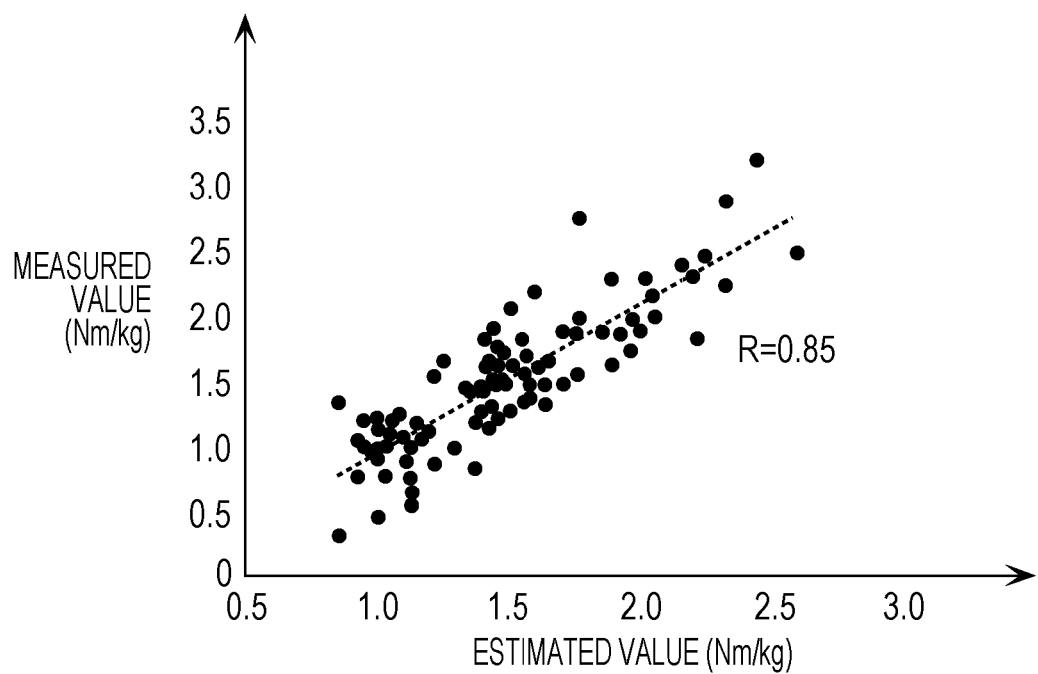
FIG. 11 is a diagram illustrating a correlation between measured values and estimated values of knee extension muscle strength of a subject.
FIG. 12 is a diagram comparatively illustrating estimation accuracy of a motor ability value achieved by an estimation method of according to an embodiment and estimation accuracy achieved by other estimation methods.

FIG. 11 illustrates an example of a result obtained when knee extension muscle strength of a subject was estimated using the estimation method according to the embodiment. More specifically, FIG. 11 illustrates a correlation between the estimated values and the actually measured values of knee extension muscle strengths for 102 subjects. In this experiment, as for the estimation knowledge, neural network regression including one intermediate layer with 32 nodes was used. The relation between the measured values of the knee extension muscle strength and the estimated values was evaluated using 6-fold cross validation. As a result of the evaluation, R=0.85 was obtained as the correlation coefficient between the measured values and the estimated values using the estimation method according to the embodiment. The obtained correlation coefficient indicates that the motor function was estimated with high accuracy.

For example, in the case where the technique disclosed in Japanese Patent No, 4696677 was used in experiments, the correlation coefficient R between the measured values and the estimated values was 0.65 in the highest case. Thus, it turns out that the estimation method according to the present embodiment can provide high accuracy in the motor function estimation.

FIG. 12 illustrates an example of an estimated motor ability value using the estimation method according to the present embodiment in comparison with examples of estimated motor ability values using other method. More specifically, FIG. 12 illustrates correlation coefficients between estimated values and measured values and average errors of estimated values with reference to actually measured values for respective estimation methods. In FIG. 12, the estimation method according to the present embodiment is compared with other two estimation methods, that is, a 6-minute walk test and a 10-m walk test. The 6-minute walk test and the 10-m walk test are methods which are widely used in clinical tests. In these methods, the walking distance achieved in 6 minutes and the walking speed achieved in walking along a distance of 10 m are employed as simple indexes of motor ability values. The 10-m walk test provides a simple method of evaluating a motor ability value by measuring the walking speed along a distance of 10 m.

In the method disclosed in Japanese Patent No. 4696677, the acceleration in the moving direction is used, and thus this method provides a similar result to that provided by the 6-minute walking distance test. In the method disclosed in Japanese Patent No. 4696677, a fixed feature value (overall walking PCA) is used. In this method, unlike the estimation method according to the embodiment, no specific feature is used, but an average walking waveform is calculated from total data obtained in 6 minutes, and the fixed feature value is calculated by PCA.

FIG. 12 also illustrates, by way of comparison, a method of estimating the lower extremity muscle strength using, as feature values, the 6-minute walking distance and the 10-m walking speed and a method of estimation using, as a feature value, the fixed feature value (overall walking PCA) wherein neural network regression is employed in both method. A result of the estimation method using the 6-minute walking distance and the 10-m walking speed as the feature values is shown in a top row in FIG. 12. A result of the estimation method using the fixed feature value (overall walking PCA) as the feature value is shown in a middle row in FIG. 12. In a bottom row of FIG. 12, shown is a result of estimation of a motor function from action sensor values such as an acceleration and the like measured in the 6-minute walking test using the estimation method according to the present embodiment.

As can be seen from FIG. 12, the method of estimating the motor ability value according to the embodiment can provides a higher estimation accuracy than can be achieved in any comparative method. That is, the method according to the embodiment makes it possible to estimate the motor function with high accuracy from data obtained in a low-load walking test.

Other Embodiments

The present disclosure has been described above with reference to the motor function estimation system and related techniques according to one or more embodiments. However, the present disclosure is not limited to those embodiments. It will be apparent to those skilled in the art that many various modifications may be applicable to the embodiments without departing from the spirit and scope of the present disclosure. Furthermore, constituent elements of different embodiments may be combined. In this case, any resultant combination also falls within the scope of the present disclosure.

For example, in the motor function estimation system 1000 disclosed above, the lower extremity motor ability value of a subject is estimated by using, by way of example but not limitation, the acceleration sensor, the heartbeat sensor, the temperature sensor, and the angular velocity sensor. Those sensors may be disposed at any locations on movable parts such as an arm or the like of a subject such that the motor function estimation system 1000 estimates motor ability values associated with the movable parts.

In the motor function estimation system 1000 according to the present disclosure, the estimation information generation apparatus 100 builds estimation knowledge using, for example, action sensor values and motor ability values of a subject. The action sensor values and the motor ability values used in building the estimation knowledge may be those obtained for one subject or a plurality of subjects. In a case where action sensor values and motor ability values are acquired for a plurality of subjects, the subjects may be many unspecific subjects. When the estimation knowledge is built using data associated with specific one subject, the estimation knowledge is dedicated to this subject, and use of the dedicated estimation knowledge allows it to output a motor ability value in which a characteristic of the subject is reflected. When the estimation knowledge is built using data obtained from many unspecific subjects, the estimation knowledge can be used for general purpose, and use of the general-purpose estimation knowledge allows it to output a motor ability value without being affected by a specific characteristic of a particular subject.

In the present disclosure, all or part of units, apparatuses, members, and elements, and all or part of functional blocks such as those shown in the block diagram of FIG. 1 may be implemented by one or more electronic circuits including a semiconductor device, a semiconductor integrated circuit (IC), an LSI (Large Scale Integration). The LSI or the IC may be integrated on a single chip or may be realized by a combination of a plurality of chips. For example, functional blocks other than storage elements may be integrated on a signal chip. The integrated circuits called the LSI or the IC herein may be called differently depending on the integration density, and integrated circuits called a system LSI, a VLSI (Very Large Scale Integration), or a ULSI (Ultra Large Scale Integration) may also be used in the present disclosure. Furthermore, a field programmable gate array (FPGA) capable of being programmed after the LSI is produced, and a reconfigurable logic device (RLD) capable of being reconfigured in terms of internal connections or capable of being set up in terms of internal circuits segments may also be used for the same purpose.

Part or all of functions or operations of units, apparatuses, members or the like may be realized by software. In this case, the software may be stored in a non-transitory storage medium. The non-transitory storage medium may be one of or a combination of a ROM, an optical disk, a hard disk drive, or the like. When the software is executed by a processor, a particular function associated with the software is executed by the processor and a peripheral apparatus. The system or the apparatus may include one or more non-transitory storage media in which software is stored, a processor, and a hardware device such as an interface.

The present disclosure allows it to easily achieve estimation of a motor ability with high accuracy by calculating a time segment and a feature useful for the estimation from action sensor values measured over a predetermined time period by a sensor worn on a subject. The technique according to the present disclosure may be used in a wide variety of applications.

What is claimed is:

1. A motor function estimation information generation apparatus comprising:
   a sensor that measures, in a predetermined time period, at least one selected from the group consisting of an acceleration, a heart rate, a body temperature, and an angular velocity of a subject; and
   a first processing circuit that performs a process,
   the process performed by the first processing circuit including
   (a1) acquiring at least one sensor value selected from the group consisting of sensor values in terms of the acceleration, the heart rate, the body temperature, and the angular velocity of the subject, and a motor ability value of the subject,
   (a2) determining a feature of the sensor value and a time segment in the predetermined time period,
   (a3) calculating, using the sensor value, a feature vector corresponding to a feature value of the feature in the time segment,
   (a4) acquiring a first weight vector for use in estimating a motor ability value using the feature vector and the motor ability value,
   (a5) calculating a gradient vector with respect to the feature vector using the first weight vector and the motor ability value,
   (a6) determining a new time segment in the predetermined time period and a new feature based on the new time segment,
   (a7) calculating, using the sensor value, a feature candidate vector that is a candidate for a feature vector corresponding to a feature value of the new feature in the new time segment,
   (a8) determining a feature candidate vector satisfying a predetermined condition based on the gradient vector, based on a difference between the feature candidate vector and the feature vector,
   (a9) correcting the first weight vector to a second weight vector using the feature candidate vector satisfying the predetermined condition, and
   (a10) storing, in a storage, a feature and a time segment corresponding to the feature candidate vector satisfying the predetermined condition and also storing the second weight vector.

2. The motor function estimation information generation apparatus according to claim 1, wherein the weight vector implements a neural network such that a connection between nodes of the neural network is weighted by the weight vector.

3. The motor function estimation information generation apparatus according to claim 1, wherein the gradient vector is a gradient vector with respect to the feature vector in terms of an index indicating an error of the motor ability value estimated using the first weight vector from the acquired motor ability value.

4. The motor function estimation information generation apparatus according to claim 1, wherein the feature candidate vector satisfying the predetermined condition is determined based on a degree of coincidence of the difference between the feature candidate vector and the feature vector with the gradient vector.

5. A motor function estimation system comprising:
the motor function estimation information generation apparatus according to claim 1, and
a second processing circuit that performs a process,
the process performed by the second processing circuit including
acquiring at least on sensor value selected from the group consisting of sensor values in terms of an acceleration, a heart rate, a body temperature, and an angular velocity of a subject,
calculating an estimated feature vector using a feature and a time segment stored in the storage and the sensor value,
estimating a motor ability value using the second weight vector stored in the storage and the estimated feature vector, and
outputting the resultant motor ability value.

6. A motor function estimation information generation method comprising:
(b1) acquiring at least one sensor value selected from the group consisting of sensor values in terms of an acceleration, a heart rate, a body temperature, and an angular velocity of a subject, and a motor ability value of the subject;
(b2) determining a feature of the sensor value and a time segment in a predetermined time period;
(b3) calculating, using the sensor value, a feature vector corresponding to a feature value of the feature in the time segment;
(b4) acquiring a first weight vector for use in estimating a motor ability value using the feature vector and the motor ability value;
(b5) calculating a gradient vector with respect to the feature vector using the first weight vector and the motor ability value;
(b6) determining a new time segment in the predetermined time period and a new feature based on the new time segment;
(b7) calculating, using the sensor value, a feature candidate vector that is a candidate for a feature vector corresponding to a feature value of the new feature in the new time segment;
(b8) determining a feature candidate vector satisfying a predetermined condition based on the gradient vector, based on a difference between the feature candidate vector and the feature vector;
(b9) correcting the first weight vector to a second weight vector using the feature candidate vector satisfying the predetermined condition; and
(b10) storing, in a storage, a feature and a time segment corresponding to the feature candidate vector satisfying the predetermined condition and also storing the second weight vector.

7. The motor function estimation information generation method according to claim 6, wherein the weight vector implements a neural network such that a connection between nodes of the neural network is weighted by the weight vector.

8. The motor function estimation information generation method according to claim 6, wherein the gradient vector is a gradient vector with respect to the feature vector in terms of an index indicating an error of the motor ability value estimated using the first weight vector from the acquired motor ability value.

9. The motor function estimation information generation method according to claim 6, wherein the feature candidate vector satisfying the predetermined condition is determined based on a degree of coincidence of the difference between the feature candidate vector and the feature vector with the gradient vector.

10. A motor function estimation method comprising:
(b1) acquiring at least one sensor value selected from the group consisting of sensor values in terms of an acceleration, a heart rate, a body temperature, and an angular velocity of a subject, and a motor ability value of the subject;
(b2) determining a feature of the sensor value and a time segment in a predetermined time period;
(b3) calculating, using the sensor value, a feature vector corresponding to a feature value of the feature in the time segment;
(b4) acquiring a first weight vector for use in estimating a motor ability value using the feature vector and the motor ability value;
(b5) calculating a gradient vector with respect to the feature vector using the first weight vector and the motor ability value;
(b6) determining a new time segment in the predetermined time period and a new feature based on the new time segment;
(b7) calculating, using the sensor value, a feature candidate vector that is a candidate for a feature vector corresponding to a feature value of the new feature in the new time segment;
(b8) determining a feature candidate vector satisfying a predetermined condition based on the gradient vector, based on a difference between the feature candidate vector and the feature vector;
(b9) correcting the first weight vector to a second weight vector using the feature candidate vector satisfying the predetermined condition;
(b10) storing, in a storage, a feature and a time segment corresponding to the feature candidate vector satisfying the predetermined condition and also storing the second weight vector;
(b11) further acquiring at least one sensor value selected from the group consisting of sensor values in terms of an acceleration, a heart rate, a body temperature, and an angular velocity of a subject;
(b12) calculating an estimated feature vector using the feature and the time segment stored in the storage and the sensor value; and
(b13) estimating a motor ability value using the second weight vector stored in the storage and the estimated feature vector.

11. A storage medium including a stored control program for causing a device having a processor to execute a process, the storage medium being non-transitory and computer-readable, the process comprising:
(b1) acquiring at least one sensor value selected from the group consisting of sensor values in terms of an acceleration, a heart rate, a body temperature, and an angular velocity of a subject, and a motor ability value of the subject;

(b2) determining a feature value of the sensor value and a time segment n a predetermined time period;

(b3) calculating, using the sensor value, a feature vector corresponding to a feature value of the feature in the time segment;

(b4) acquiring a first weight vector for use in estimating a motor ability value using the feature vector and the motor ability value;

(b5) calculating a gradient vector with respect to the feature vector using the first weight vector and the motor ability value;

(b6) determining a new time segment in the predetermined time period and a new feature value based on the new time segment;

(b7) calculating, using the sensor value, a feature candidate vector that is a candidate for a feature vector corresponding to a feature value of the new feature in the new time segment;

(b8) determining a feature candidate vector satisfying a predetermined condition based on the gradient vector, based on a difference between the feature candidate vector and the feature vector;

(b9) correcting the first weight vector to a second weight vector using the feature candidate vector satisfying the predetermined condition; and (b10) storing, in a storage, a feature and a time segment corresponding to the feature candidate vector satisfying the predetermined condition and also storing the second weight vector.

12. The storage medium according to claim 11, wherein the weight vector implements a neural network such that a connection between nodes of the neural network is weighted by the weight vector.

13. The storage medium according to claim 11, wherein the gradient vector is a gradient vector with respect to the feature vector in terms of an index indicating an error of the motor ability value estimated using the first weight vector from the acquired motor ability value.

14. The storage medium according to claim 11, wherein the feature candidate vector satisfying the predetermined condition is determined based on a degree of coincidence of the difference between the feature candidate vector and the feature vector with the gradient vector.

15. A storage medium including a stored control program for causing a device having a processor to execute a process, the storage medium being non-transitory and computer-readable, the process comprising:

(b1) acquiring at least one sensor value selected from the group consisting of sensor values in terms of an acceleration, a heart rate, a body temperature, and an angular velocity of a subject, and a motor ability value of the subject;

(b2) determining a feature value of the sensor value and a time segment in a predetermined time period;

(b3) calculating, using the sensor value, a feature vector corresponding to a feature value of the feature in the time segment;

(b4) acquiring a first weight vector for use in estimating a motor ability value, using the feature vector and the motor ability value;

(b5) calculating a gradient vector with respect to the feature vector using the first weight vector and the motor ability value;

(b6) determining a new time segment in the predetermined time period and a new feature value based on the new time segment;

(b7) calculating, using the sensor value, a feature candidate vector that is a candidate for a feature vector corresponding to the feature value of the new feature in the new time segment;

(b8) determining a feature candidate vector satisfying a predetermined condition based on the gradient vector, based on a difference between the feature candidate vector and the feature vector;

(b9) correcting the first weight vector to a second weight vector using the feature candidate vector satisfying the predetermined condition;

(b10) storing, in a storage, a feature and a time segment corresponding to the feature candidate vector satisfying the predetermined condition and also storing the second weight vector;

(b11) further acquiring at least one sensor value selected from the group consisting of sensor values in terms of an acceleration, a heart rate, a body temperature, and an angular velocity of a subject;

(b12) calculating an estimated feature vector using the feature and the time segment stored in the storage and the sensor value; and (b13) estimating a motor ability value using the second weight vector stored in the storage and the estimated feature vector.

16. A motor function estimation information generation apparatus comprising:

a sensor that measures, in a predetermined time period, at least one selected from the group consisting of an acceleration, a heart rate, a body temperature, and an angular velocity of a subject; and a first processing circuit that performs a process, the process performed by the first processing circuit including (a1) acquiring at least one sensor value selected from the group consisting of sensor values in terms of the acceleration, the heart rate, the body temperature, and the angular velocity of the subject, and a motor ability value of the subject, (a2) determining a feature of the sensor value and a time segment in the predetermined time period, (a3) calculating, using the sensor value, a feature vector corresponding to a feature value of the feature in the time segment, (a4) acquiring a first weight vector for use in estimating a motor ability value using the feature vector and the motor ability value, (a5) calculating a gradient vector with respect to the feature vector using the first weight vector and the motor ability value, (a6) determining a new time segment in the predetermined time period, (a7) calculating, using the sensor value, a feature candidate vector that is a candidate for a feature vector corresponding to a feature value of the feature in the new time segment, (a8) determining a feature candidate vector satisfying a predetermined condition based on the gradient vector, based on a difference between the feature candidate vector and the feature vector, (a9) correcting the first weight vector to a second weight vector using the feature candidate vector satisfying the predetermined condition, and (a10) storing, in a storage, a time segment corresponding to the feature candidate vector satisfying the predetermined condition and also storing the second weight vector.

17. A motor function estimation information generation method comprising:
(b1) acquiring at least one sensor value selected from the group consisting of sensor values in terms of an acceleration, a heart rate, a body temperature, and an angular velocity of a subject, and a motor ability value of the subject;
(b2) determining a feature of the sensor value and a time segment in a predetermined time period;
(b3) calculating, using the sensor value, a feature vector corresponding to a feature value of the feature in the time segment;
(b4) acquiring a first weight vector for use in estimating a motor ability value using the feature vector and the motor ability value;
(b5) calculating a gradient vector with respect to the feature vector using the first weight vector and the motor ability value;
(b6) determining a new time segment in the predetermined time period;
(b7) calculating, using the sensor value, a feature candidate vector that is a candidate for a feature vector corresponding to a feature value of the feature in the new time segment;
(b8) determining a feature candidate vector satisfying a predetermined condition based on the gradient vector, based on a difference between the feature candidate vector and the feature vector;
(b9) correcting the first weight vector to a second weight vector using the feature candidate vector satisfying the predetermined condition; and
(b10) storing, in a storage, a time segment corresponding to the feature candidate vector satisfying the predetermined condition and also storing the second weight vector.

* * * * *